United States Patent
Miyamoto et al.

(10) Patent No.: US 9,333,158 B2
(45) Date of Patent: May 10, 2016

(54) SPRAY BASE MATERIAL INCLUDING LOW-MOLECULAR GELATOR

(75) Inventors: Misao Miyamoto, Chiyoda-ku (JP); Takehisa Iwama, Funabashi (JP); Nobuhide Miyachi, Chiyoda-ku (JP); Masahiro Gotoh, Fukuoka (JP)

(73) Assignees: NISSAN CHEMICAL INDUSTRIES, LTD., Tokyo (JP); KYUSHU UNIVERSITY, Fukuoka-shi (JP)

(*) Notice: Subject to any disclaimer, the term of this patent is extended or adjusted under 35 U.S.C. 154(b) by 321 days.

(21) Appl. No.: 13/256,765

(22) PCT Filed: Mar. 12, 2010

(86) PCT No.: PCT/JP2010/054231
§ 371 (c)(1),
(2), (4) Date: Oct. 21, 2011

(87) PCT Pub. No.: WO2010/106981
PCT Pub. Date: Sep. 23, 2010

(65) Prior Publication Data
US 2012/0035108 A1  Feb. 9, 2012

(30) Foreign Application Priority Data

Mar. 16, 2009 (JP) ................ 2009-063039
Jun. 19, 2009 (JP) ................ 2009-147073

(51) Int. Cl.
*A61K 8/64* (2006.01)
*A61K 38/05* (2006.01)
*A61K 8/04* (2006.01)
*A61K 9/70* (2006.01)
*A61Q 19/00* (2006.01)

(52) U.S. Cl.
CPC . *A61K 8/64* (2013.01); *A61K 8/046* (2013.01); *A61K 9/7015* (2013.01); *A61K 38/05* (2013.01); *A61Q 19/00* (2013.01); *A61K 2800/48* (2013.01)

(58) Field of Classification Search
CPC ....... A61K 47/00; A61K 8/64; A61K 9/0014; A61K 8/042; A61K 49/0054; A61K 8/65; C07K 14/00
See application file for complete search history.

(56) References Cited

U.S. PATENT DOCUMENTS 5,503,776 A * 4/1996 Murase et al. ................ 252/397
2005/0142092 A1 6/2005 Lintner 2007/0203062 A1 8/2007 Ellis-Behnke et al.
2009/0111734 A1 4/2009 Ellis-Behnke et al.
2010/0291210 A1* 11/2010 Miyachi et al. ............... 424/484

FOREIGN PATENT DOCUMENTS

| JP | A-09-241115 | 9/1997 |
| JP | A-2000-051682 | 2/2000 |
| JP | A-2000-229255 | 8/2000 |
| JP | A-2000-351726 | 12/2000 |
| JP | A-2001-072999 | 3/2001 |
| JP | A-2001-089359 | 4/2001 |
| JP | A-2003-147333 | 5/2003 |
| JP | A-2003-238387 | 8/2003 |
| JP | A-2008-539257 | 11/2008 |
| WO | WO 2009/005151 A1 | 1/2009 |
| WO | WO 2009/005152 A1 | 1/2009 |
| WO | WO 2010/013555 A1 | 2/2010 |
| WO | WO 2010013555 A1 * | 2/2010 |

OTHER PUBLICATIONS

Machine translation for WO 2010/0013555; published Feb. 4, 2010; machine translation obtained Nov. 26, 2013 from the JPO/INPI; JP,2010/013555,A1; pp. 1-35.*
Machine translation for WO 2009/005151; published Jan. 8, 2009; machine translation obtained Nov. 26, 2013 from the JPO/INPI; JP,2009/005151,A1; pp. 1-22.*
Kar et al., "Organogelation and Hydrogelation of Low-Molecular-Weight Amphiphilic Dipeptides: pH Responsiveness in Phase-Selective Gelation and Dye Removal," *Langmuir*, vol. 25, No. 15, pp. 8639-8648, 2009.
Matsumoto et al., "Dojin News," *Property of the National Library of Medicine*, No. 118, pp. 1-16, Apr. 28, 2006.
Estroff et al., "Water Gelation by Small Organic Molecules," *Chemical Reviews*, vol. 104, No. 3, pp. 1201-1217, 2004.
Suzuki et al., "Supramolecular Hydrogels Formed by L-Lysine Derivatives," *Chemistry Letters*, vol. 33, No. 11, pp. 1496-1497, 2004.
Jung et al., "Self-Assembly of a Sugar-Based Gelator in Water: Its Remarkable Diversity in Gelation Ability and Aggregate Structure," *Langmuir*, vol. 17, No. 23, pp. 7229-7232, 2001.
Hamachi et al., "Solid phase lipid synthesis (SPLS) for construction of an artificial glycolipid library," *Chemistry Communications*, pp. 1281-1282, 2000.
Suzuki et al., "Supramolecular hydrogel formed by glucoheptonamide of L-lysine: simple preparation and excellent hydrogelation ability," *Tetrahedron*, vol. 63, pp. 7302-7308, 2007.
Matsuzawa et al., "Assembly and Photoinduced Organization of Mono- and Oligopeptide Molecules Containing an Azobenzene Moiety," *Advanced Functional Materials*, vol. 17, pp. 1507-1514, 2007.
International Search Report issued in Application No. PCT/JP2010/054231; Dated Jun. 15, 2010 (With Translation).

* cited by examiner

Primary Examiner — Lianko Garyu
(74) Attorney, Agent, or Firm — Oliff PLC

(57) ABSTRACT

A spray base material containing an aqueous medium that is gelled by a low-molecular gelator in the medium, wherein the low-molecular gelator includes one or more compounds selected from low-molecular compounds capable of gelling the aqueous medium via self-assembly.

19 Claims, 2 Drawing Sheets

SPRAY BASE MATERIAL INCLUDING LOW-MOLECULAR GELATOR

TECHNICAL FIELD

The present invention relates to a spray base material, and specifically to a spray base material including an aqueous medium that is gelled by a low-molecular gelator in the medium, in which the low-molecular gelator includes one, two, or more compounds selected from a group consisting of low-molecular compounds that can gel the aqueous medium via self-assembly, the spray base material being sprayable as gel without dripping, and a liquid drop of the spray base material readily gelling on a sprayed surface after spraying so that dripping is less likely to occur.

The spray base material of the present invention can be suitably utilized as spray base materials for skin care products, hair care products, pharmaceuticals for external use, fragrances, deodorants, insect repellents, insecticides, agrochemicals, detergents, paints, antistatic coatings, and preservatives, and base materials for forming coatings and thin films.

BACKGROUND ART

In recent years, spray products are applied to various fields, and many of these products are spray preparations obtained by mixing a mother liquid in a liquid state with a formulation that has a desired use. Prescribed properties desired for these spray products generally include (1) that excellent spraying can be achieved under any environment, (2) that a drop of the mother liquid excellently fixes to a sprayed surface without causing ununiform spraying, (3) that dripping of the mother liquid is less likely to occur on a vertical surface and an inclined surface, and (4) that a drop of the mother liquid causes no damage to a sprayed surface (skin and the like, in particular) for a prolonged period of time after the drop of the mother liquid is dried and fixed, which means the spray product is safe, and the like.

To fulfill these prescribed properties (1) to (3), various techniques have been developed until now.

For example, a technique has been developed for (3) preventing dripping by dissolving polymer thickener in a mother liquid to increase the viscosity of the mother liquid [Patent Document 1]. However, in the case of a solution of an ordinary macromolecular compound, spraying itself may be impossible when the viscosity of mother liquid is high enough to effectively prevent dripping. In order to achieve sucking into a nozzle and to maintain sprayability, the viscosity of mother liquid should be designed to be low enough, which in turn cannot adequately prevent dripping. In other words, to achieve both dripping prevention and smooth spraying is crucial. However, optimization of viscosity of mother liquid to that end has been extremely difficult. In addition, a solution of a macromolecular compound has a typical characteristic (spinnability) to easily form threads during spraying and, therefore, ideal mist in which liquid drops are independent from each other cannot be obtained. Thus, mist formation is significantly poor as compared to the case with no thickener, resulting in ununiform spraying. That is also a problem.

Many attempts have been made, in order to enhance the properties (2) and (3), to formulate a surfactant in a mother liquid to achieve thickening via formation of a micellar structure in an aqueous phase and to control the surface tension of a sprayed drop of the mother liquid [Patent Documents 2, 3].

However, for example, the mother liquid has fluidity, and therefore, it cannot be sprayed when inverted. Thus, the property (1) cannot be successfully achieved. In addition, when the surfactant content is increased in order to enhance dripping prevention, in the case of spray for skin, for example, skin irritation is likely to develop, which is inconvenient in terms of safety as of (4). That is another problem.

To fulfill the prescribed properties (1) and (3), enhancement in the structure of a container has been developed (Patent Document 4, for example). In these instances, thin mist that is fixed on a coated surface achieves an excellent result. However, heavy spraying, namely thick coating, causes dripping. Therefore, a problem in dripping prevention has not been substantially solved.

As techniques that achieve the prescribed properties (1) to (4) in a relatively good balance, sprays containing a gel composition have been disclosed in which the gel composition is predominantly composed of hectorite that is constituted of hydrophilic smectite (Patent Document 5, Patent Document 6). However, these techniques disclosed have problems that the spray is mainly composed of inorganic substances with poor track records of safety use and that the hectorite aggregates in a main dispersion medium of the spray composition, such as alcohols, to lead a decrease in spraying properties.

Under these circumstances, a spray that utilizes cellulose dispersion has been developed focusing on its sprayability, foam-forming ability, foam-retention, thixotropy, and dispersion stability. However, cellulose has poor compatibility with fat-soluble agents and other surfactants and is likely to cause phase separation. Therefore application thereof to pharmaceuticals for external use, cosmetics, and agrochemical preparations is difficult.

In practical use, a spray preparation that can form mist capable of inclusion/sustained release of a plurality of compounds is required. For example, pharmaceuticals for external use and cosmetics may require dissolving both a hydrophilic compound and a hydrophobic compound, and chemical treatment is then needed to, for example, introduce a hydrophilic functional group into the hydrophobic compound. None of the conventional techniques mentioned above has suggested a material that fulfills both performance as a spray base material and practically requisite performance such as inclusion/sustained release of compounds.

On the other hand, hydrogel is used in various fields as a highly biocompatible material having water as a medium, and various studies have been conducted on hydrogel that includes a macromolecular compound and hydrogel that is obtained via self-assembly of low-molecular compounds.

Polymer gel (chemical gel and physical gel) that is obtained by crosslinking of macromolecular compounds via a covalent bond, an ionic bond, a hydrogen bond, or the like can prevent leakage of liquid from a container during spraying via solidification of solution which is useful. However, chemical polymer gel resulting from chemical crosslinking is difficult to spray as gel, and most of physical polymer gel is not sprayable. Even a sprayable polymer gel cannot achieve inclusion/sustained release of low-molecular compounds such as drugs, and its poor compatibility with the drugs, etc. and other additives leads phase separation, which is a problem.

In research on a low-molecular hydrogelator including a low-molecular compound, determination of a mechanism of self-organization among low-molecular compounds in water and molecular design are difficult, but the functions of the low-molecular hydrogelator have attracted a lot of interest, which lead active research on that in recent years. As a result, some low-molecular hydrogelators have been discovered

[Non-patent Documents 1, 2]. Most of them are amphiphilic compounds that have both a long-chain alkyl group as a hydrophobic moiety and a hydrophilic moiety, and examples of these include ones having an amino acid [Non-patent Document 3], ones having a peptide [Patent Documents 7, 8], ones having a mono- or polysaccharide [Non-patent Documents 4, 5], and ones having a polyol [Non-patent Document 6], as the hydrophilic moiety. A low-molecular gelator has been developed utilizing the fact that a peptide including valine easily assumes a β-sheet structure [Non-patent Document 7].

Low-molecular hydrogelators that gel aqueous alcohol solutions and/or organic solvent aqueous solutions or that cannot gel water alone nor organic solvent alone but gel aqueous alcohol solutions and/or organic solvent aqueous solutions have been reported. A well-known common characteristic of low-molecular gel is to quickly react to external stress to convert from gel to sol.

DISCLOSURE OF THE INVENTION

Problem to be Solved by the Invention

As described above, no spray base material has been developed until now that fulfills the prescribed properties (1) to (4) regarding spray performance and safety, that is excellent in compatibility with various agents to be sprayed and additives, and that adequately fulfills performance of forming mist capable of inclusion/sustained release of a plurality of compounds.

Even in the case of hydrogel that is a highly biocompatible material, the performance above is not adequately fulfilled by a hydrogel including a macromolecular compound, and no spray base material has been developed that is made with a hydrogel including a low-molecular compound.

The present invention is devised based on the above circumstances, and an object of the present invention is to provide a spray base material that can be safely used with a sense of security, namely, for example, that prevents leakage of liquid from a spray container, that is sprayable under any ordinary possible condition of use (when inverted, for example), that is sprayable to achieve uniform coating of the surface of an object (surface to be sprayed) without scattering, that causes no dripping from a sprayed surface, and that is safe when sprayed on a skin surface and the like. Furthermore, an object of the present invention is to provide a spray base material with an excellent sprayability that can include both hydrophilic and hydrophobic low-molecular compounds such as physiologically active compounds and perfume components to be used in pharmaceuticals, agrochemicals, and cosmetics, and that has a sustained release property.

Means for Solving the Problem

The inventors of the present invention have conducted intensive research to solve the problems and, as a result, achieved the present invention.

Namely, as a first aspect, a spray base material includes an aqueous medium that is gelled by a low-molecular gelator in the medium, in which the low-molecular gelator includes one, two, or more compounds selected from a group consisting of low-molecular compounds capable of gelling the aqueous medium via self-assembly.

As a second aspect, the spray base material according to the first aspect is characterized in that the molecular weight of the low-molecular compound is not higher than 1000.

As a third aspect, the spray base material according to the second or the third aspect is characterized in that the concentration of the low-molecular compound in the gelled aqueous medium is 0.0001 to 20% (w/v).

As a fourth aspect, the spray base material according to any one of the first to the third aspects is characterized in that the low-molecular compound contains a hydrophobic moiety and a hydrophilic moiety.

As a fifth aspect, the spray base material according to any one of claims 1 to 4 is characterized in that the low-molecular compound includes a lipid peptide of Formula (1):

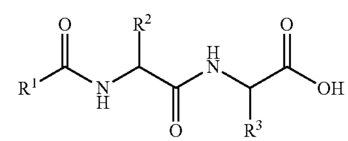

(1)

(where $R^1$ is a $C_{9-23}$ aliphatic group, $R^2$ is a hydrogen atom or a $C_{1-4}$ alkyl group that optionally contains a $C_{1-2}$ branched chain, $R^3$ is a $-(CH_2)_n-X$ group, n is a number of 1 to 4, and X is an amino group, a guanidino group, a $-CONH_2$ group, a 5-membered ring optionally containing 1 to 3 nitrogen atoms, a 6-membered ring optionally containing 1 to 3 nitrogen atoms, or a condensed heterocycle that contains a 5-membered ring and a 6-membered ring optionally containing 1 to 3 nitrogen atoms), or a pharmaceutically usable salt thereof.

As a sixth aspect, the spray base material according to the fifth aspect is characterized in that in Formula (1), $R^3$ is a $-(CH_2)_n-X$ group, n is a number of 1 to 4, and X is an amino group, a guanidino group, a $-CONH_2$ group, a 5-membered ring optionally containing 1 or 2 nitrogen atoms, or a condensed heterocycle that contains a 5-membered ring and a 6-membered ring optionally containing 1 or 2 nitrogen atoms.

As a seventh aspect, the spray base material according to the fifth aspect is characterized in that in Formula (1), $R^1$ is a linear $C_{11-21}$ aliphatic group that optionally contains 0 to 2 unsaturated bonds.

As an eighth aspect, the spray base material according to the fifth aspect is characterized in that in Formula (1), $R^2$ is a hydrogen atom or a $C_{1-3}$ alkyl group that optionally contains a $C_1$ branched chain.

As a ninth aspect, the spray base material according to the sixth aspect is characterized in that in Formula (1), n is a number of 1 to 4 and X is an amino group, a guanidino group, or a $-CONH_2$ group, or n is 1 and X is a pyrrole group, an imidazole group, a pyrazole group, or an imidazole group.

As a tenth aspect, the spray base material according to any one of the first to the ninth aspects is characterized by further containing a physiologically active substance or a functional substance.

As an 11th aspect, a thin film includes one, two, or more compounds selected from a group consisting of low-molecular compounds capable of gelling an aqueous medium via self-assembly, and the aqueous medium.

As a 12th aspect, the thin film according to the 11th aspect is characterized in that the self-assembly has a fibrous structure.

As a 13th aspect, a process for preparing a thin film is characterized by including applying the spray base material as described in any one of the first to the tenth aspects by a spray method.

As a 14th aspect, a sol obtained by mechanically disintegrating an aqueous medium that is gelled by a low-molecular gelator in the medium, in which the low-molecular gelator includes one, two, or more compounds selected from a group consisting of low-molecular compounds capable of gelling the aqueous medium via self-assembly.

As a 15th aspect, a spray base material is characterized by including the sol.

As a 16th aspect, the spray base material according to claim 15 is characterized in that the low-molecular compound included in the low-molecular gelator used in the formation of the sol includes a lipid peptide of Formula (1):

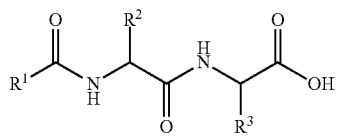

(1)

(where $R^1$ is a $C_{9\text{-}23}$ aliphatic group, $R^2$ is a hydrogen atom or a $C_{1\text{-}4}$ alkyl group that optionally contains a $C_{1\text{-}2}$ branched chain, $R^3$ is a —$(CH_2)_n$—X group, n is a number of 1 to 4, and X is an amino group, a guanidino group, a —$CONH_2$ group, a 5-membered ring optionally containing 1 to 3 nitrogen atoms, a 6-membered ring optionally containing 1 to 3 nitrogen atoms, or a condensed heterocycle that contains a 5-membered ring and a 6-membered ring optionally containing 1 to 3 nitrogen atoms), or a pharmaceutically usable salt thereof.

As a 17th aspect, the spray base material according to the 16th aspect is characterized in that in Formula (1), $R^3$ is a —$(CH_2)_n$—X group, n is a number of 1 to 4, and X is an amino group, a guanidino group, a —$CONH_2$ group, a 5-membered ring optionally containing 1 or 2 nitrogen atoms, or a condensed heterocycle that contains a 5-membered ring and a 6-membered ring optionally containing 1 or 2 nitrogen atoms.

As an 18th aspect, the spray base material according to the 16th aspect is characterized in that in Formula (1), $R^1$ is a linear $C_{11\text{-}21}$ aliphatic group that optionally contains 0 to 2 unsaturated bonds.

As a 19th aspect, the spray base material according to the 16th aspect is characterized in that in Formula (1), $R^2$ is a hydrogen atom or a $C_{1\text{-}3}$ alkyl group that optionally contains a $C_1$ branched chain.

As a 20th aspect, the spray base material according to the 17th aspect is characterized in that in Formula (1), n is a number of 1 to 4 and X is an amino group, a guanidino group, or a —$CONH_2$ group, or n is 1 and X is a pyrrole group, an imidazole group, a pyrazole group, or an imidazole group.

As a 21st aspect, a sol includes the compound of Formula (1) and an aqueous medium.

As a 22nd aspect, a spray base material is characterized by including the sol as described in the 21st aspect.

As a 23rd aspect, the spray base material according to any one of the first to the fourth aspects is characterized in that the low-molecular compound includes a lipid peptide of Formula (2):

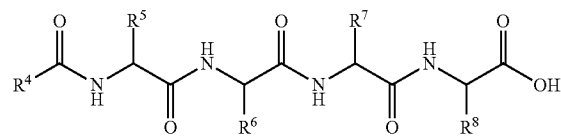

(2)

(where $R^4$ is a $C_{9\text{-}23}$ aliphatic group, $R^5$ to $R^8$ each are a hydrogen atom, a $C_{1\text{-}4}$ alkyl group that optionally contains a $C_{1\text{-}2}$ branched chain, or a —$(CH_2)_n$—X group, and at least one or more of $R^5$ to $R^8$ is a —$(CH_2)_n$—X group, n is a number of 1 to 4, and X is an amino group, a guanidino group, a —$CONH_2$ group, a 5-membered ring optionally containing 1 to 3 nitrogen atoms, a 6-membered ring optionally containing 1 to 3 nitrogen atoms, or a condensed heterocycle that contains a 5-membered ring and a 6-membered ring optionally containing 1 to 3 nitrogen atoms), or a pharmaceutically usable salt thereof.

EFFECTS OF THE INVENTION

The spray base material of the present invention is a spray base material obtained by gelling an aqueous medium (water, an aqueous solution, an aqueous alcohol solution, and/or an organic solvent aqueous solution) using a low-molecular gelator. By gelling the aqueous medium, leakage of liquid from a spray container can be prevented.

The gel formation mechanism of the low-molecular gelator used in the spray base material of the present invention is totally different from the gel formation mechanisms of commercial polymer hydrogels. That is to say, a low-molecular compound that is included in the low-molecular gelator self-assembles to form a fibrous configuration, and then the fibers form a network structure, resulting in the network structure to enclose water, various aqueous solutions, aqueous alcohol solutions, and organic solvent aqueous solutions, and the like to form gel. The "self-assembly" herein refers to that, in a group of substances (molecules) that is initially in a random state, the molecules spontaneously assemble via a non-covalent interaction between them or a similar interaction under a suitable external condition to form a macro functional assembly.

Thus, a gel obtained with the low-molecular gelator used in the spray base material of the present invention immediately converts from gel into a sol with adequate stress applied thereto, and the sol can pass through a narrow tube such as a spray nozzle.

Namely, by adding the low-molecular gelator to water, various aqueous solutions, and the like, a spray base material that is sprayable as gel in a solid state can be prepared.

As a result, even when inverted, the base material remains at the bottom of a container due to the solid state of gel, which makes spraying possible. Thus, the prescribed property (1) can be fulfilled. In other words, a base material that is sprayable under any environment can be prepared.

A low-molecular gel that is the spray base material of the present invention maintains a self-assembly structure, namely the fibrous configuration, after converting from gel into a sol with stress applied, and the network structure made by the fibrous configuration also remains to some extent without being destructed. Because of this, the material is sprayable to achieve uniform coating of a certain area with no excess scattering of the material. In addition, because the self-assembled fibrous configuration and the network structure remain right after spraying, the material converts into gel on the surface to which the material adheres, and remains gel when the adhesion surface is inclined. Thus, dripping can be prevented. In this way, by using the low-molecular gelator, a spray base material that fulfills the prescribed properties (2) and (3) can be provided.

The low-molecular gelator used in the spray base material of the present invention is a safe low-molecular gelator containing a hydrophobic moiety and a hydrophilic moiety both of which are constituted of natural substances such as fatty acids and dipeptides. Thus, a spray base material that fulfills the prescribed property (4) can be provided.

As described above, the spray base material of the present invention contains a gel that is formed with self-assembled fibers and a network structure resulting from the assembly. The gel can take in low-molecular compounds such as physiologically active substances, perfume components, pigments, and dyes inside the fibers under hydrophobic environment in the case of a hydrophobic low-molecular compound, or in an aqueous phase within the network structure in the case of a hydrophilic compound. In particular, a hydrophilic compound having a polar functional group can be adhered to the fiber surface. That is, the spray base material of the present invention allows inclusion of various hydrophilic and hydrophobic components such as medicinal components within the base material, and also allows retention on an adhesion surface (adhesive surface) or sustained release of necessary components after spraying.

As for the spray base material of the present invention, the self-assembly, namely the fibrous configuration, of the low-molecular gelator and the network structure do not disintegrate even when the spray base material is prepared using the low-molecular gelator in an amount insufficient to allow gelation or even when the gel disintegrates (into a sol) due to physical factors such as stress. Because of this, the spray base material of the present invention works as a spray base material while fully maintaining its performance to dissolve and allow inclusion of low-molecular compounds such as physiologically active substances, perfume components, pigments, and dyes, prevents scattering on spraying, and allows uniform surface coating without causing dripping from a coated area.

The low-molecular gelator used in the spray base material of the present invention can also gel an aqueous solution that dissolves an acid and a base and, therefore, the spray base material of the present invention can be used as a spray base material for the aqueous solution. In particular, the spray base material of the present invention can be prepared as a spray base material for a solution, which has a moisture-retaining and/or moisturizing effect, the pH of which is adjustable depending on the skin and the use, and examples of which include a buffer solution made by adding to potassium lactate lactic acid, which has an effect of recovering a moisture content on a skin surface.

As described above, the spray base material including a low-molecular gel obtained by the present invention can achieve excellent spraying and is safe for living organisms and the environment. In addition, the spray base material can include both hydrophilic and hydrophobic low-molecular compounds such as physiologically active compounds and perfume components to be used in pharmaceuticals, agrochemicals, and cosmetics, and also has a sustained release property. Therefore, the spray base material has wide applications in spray base materials for wound dressings that are capable of recognizing an affected area or a lesion area, anti-adhesion membranes, drug-quick delivery systems, skin care products, hair care products, pharmaceuticals for external use, fragrances, deodorants, insect repellents, insecticides, and agrochemicals, base materials for detergents, paints, antistatic coatings, and preservatives, base materials for forming coatings and thin films, and the like.

BEST MODES FOR CARRYING OUT THE INVENTION

Figure 1:
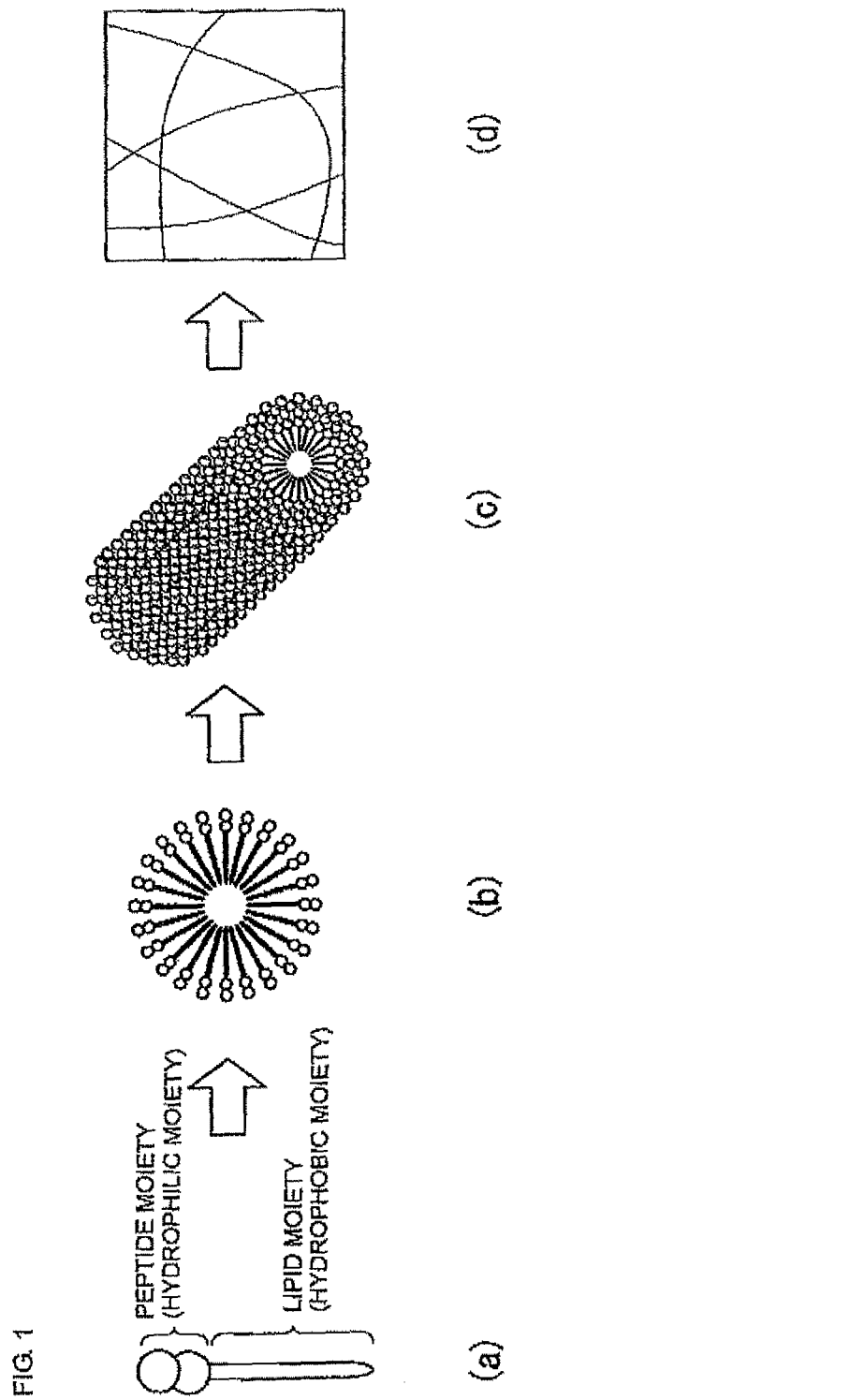
FIG. 1 is a conceptual view of self-assembly of a lipid peptide and gelation that follows.
Figure 2:
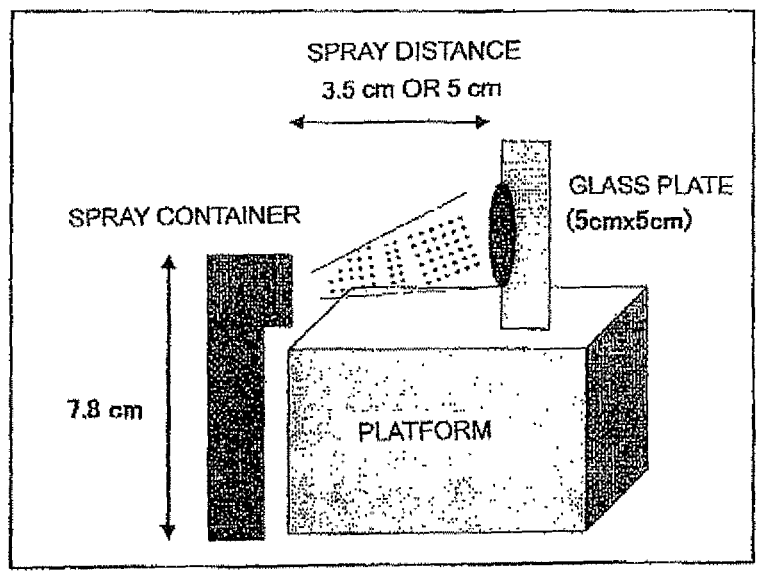
FIG. 2 is shows a device for evaluating the application properties of sprays prepared in Examples.

The spray base material of the present invention is a spray base material including an aqueous medium that is gelled by a low-molecular gelator in the medium, in which the low-molecular gelator includes one, two, or more compounds selected from a group consisting of low-molecular compounds that can gel the aqueous medium via self-assembly.

As the low-molecular gelator, a low-molecular compound that preferably has a molecular weight of not higher than 1000 and in particular contains a lipid moiety as a hydrophobic moiety and a peptide moiety as a hydrophilic moiety (namely, a so-called lipid peptide or a pharmaceutically usable salt thereof) can be used.

Examples of the low-molecular compounds containing a hydrophobic moiety and a hydrophilic moiety can include a lipid peptide of Formula (1), and the lipid peptide contains a lipid moiety (an alkylcarbonyl group) having a highly fat-soluble chain and a peptide moiety (a dipeptide, a tripeptide, or a tetrapeptide).

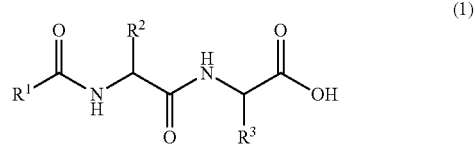

(1)

In Formula (1), $R^1$ in the lipid moiety is a $C_{9-23}$ aliphatic group, and $R^1$ is preferably a linear $C_{11-23}$ aliphatic group that optionally contains 0 to 2 unsaturated bonds.

Specific examples of the lipid moieties (acyl groups) including $R^1$ and an adjacent carbonyl group can include a lauroyl group, a dodecylcarbonyl group, a myristoyl group, a tetradecylcarbonyl group, a palmitoyl group, a margaroyl group, an oleoyl group, an elaidoyl group, a linoleoyl group, a stearoyl group, a vaccenoyl group, an octadecylcarbonyl group, an arachidoyl group, an eicosylcarbonyl group, a behenoyl group, an erucanoyl group, a docosylcarbonyl group, a lignoceyl group, a nervonoyl group, and the like, and particularly preferably include a lauroyl group, a myristoyl group, a palmitoyl group, a margaroyl group, a stearoyl group, an oleoyl group, an elaidoyl group, and a behenoyl group.

In Formula (1), $R^2$ in the peptide moiety is a $C_{1-4}$ alkyl group that optionally contains a $C_{1-2}$ branched chain.

The $C_{1-4}$ alkyl group that optionally contains a $C_{1-2}$ branched chain means an alkyl group that contains a $C_{1-4}$ main chain and optionally contains a $C_{1-2}$ branched chain, and specific examples thereof include a methyl group, an ethyl group, an n-propyl group, an isopropyl group, an n-butyl group, an isobutyl group, a sec-butyl group, a tert-butyl group, and the like.

$R^2$ is preferably a hydrogen atom or a $C_{1-3}$ alkyl group that optionally contains a $C_1$ branched chain, and is more preferably a hydrogen atom.

The $C_{1-3}$ alkyl group that optionally contains a $C_1$ branched chain means an alkyl group that contains a $C_{1-3}$ main chain and optionally contains a $C_1$ branched chain, and specific examples thereof include a methyl group, an ethyl group, an n-propyl group, an isopropyl group, an isobutyl group, a sec-butyl group, and the like. The $C_{1-3}$ alkyl group that optionally contains a $C_1$ branched chain is preferably a methyl group, an isopropyl group, an isobutyl group, or a sec-butyl group.

In Formula (1), $R^3$ is a —$(CH_2)$n-X group.

In the —$(CH_2)$n-X group, n is a number of 1 to 4, and X is an amino group, a guanidino group, a —$CONH_2$ group, a 5-membered ring optionally containing 1 to 3 nitrogen atoms, a 6-membered ring optionally containing 1 to 3 nitrogen atoms, or a condensed heterocycle that contains a 5-membered ring and a 6-membered ring optionally containing 1 to 3 nitrogen atoms.

In the —$(CH_2)$n-X group, X is preferably an amino group, a guanidino group, a —$CONH_2$ group, a pyrrole group, an imidazole group, a pyrazole group, or an indole group, and is more preferably an imidazole group. In the —$(CH_2)$n-X group, n is preferably 1 or 2 and is more preferably 1.

Accordingly, the —$(CH_2)_n$— group is preferably an aminomethyl group, a 2-aminoethyl group, a 3-aminopropyl group, a 4-aminobutyl group, a carbamoylmethyl group, a 2-carbamoylethyl group, a 3-carbamoylbutyl group, a 2-guanidinoethyl group, a 3-guanidinobutyl group, a pyrrole methyl group, an imidazole methyl group, a pyrazole methyl group, or a 3-indole methyl group, is more preferably a 4-aminobutyl group, a carbamoylmethyl group, a 2-carbamoylethyl group, a 3-guanidinobutyl group, an imidazole methyl group, or a 3-indole methyl group, and is further preferably an imidazole methyl group.

As for the compound of Formula (1), a lipid peptide that is particularly preferable as the low-molecular gelator is the following compounds faulted from a lipid moiety and a peptide moiety (a moiety of assembled amino acids). Amino acid abbreviations are as follows: alanine (Ala), asparagine (Asn), glutamine (GM), glycine (Gly), histidine (His), isoleucine (Ile), leucine (Leu), lysine (Lys), tryptophan (Trp), and valine (Val). Lauroyl-Gly-His, lauroyl-Gly-Gln, lauroyl-Gly-Asn, lauroyl-Gly-Trp, lauroyl-Gly-Lys, lauroyl-Ala-His, lauroyl-Ala-Gln, lauroyl-Ala-Asn, lauroyl-Ala-Trp, and lauroyl-Ala-Lys; myristoyl-Gly-His, myristoyl-Gly-Gln, myristoyl-Gly-Asn, myristoyl-Gly-Trp, myristoyl-Gly-Lys, myristoyl-Ala-His, myristoyl-Ala-Gln, myristoyl-Ala-Asn, myristoyl-Ala-Trp, and myristoyl-Ala-Lys; palmitoyl-Gly-His, palmitoyl-Gly-Gln, palmitoyl-Gly-Asn, palmitoyl-Gly-Trp, palmitoyl-Gly-Lys, palmitoyl-Ala-His, palmitoyl-Ala-Gln, palmitoyl-Ala-Asn, palmitoyl-Ala-Trp, and palmitoyl-Ala-Lys; and stearoyl-Gly-His, stearoyl-Gly-Gln, stearoyl-Gly-Asn, stearoyl-Gly-Trp, stearoyl-Gly-Lys, stearoyl-Ala-His, stearoyl-Ala-Gln, stearoyl-Ala-Asn, stearoyl-Ala-Trp, and stearoyl-Ala-Lys.

Most preferable examples thereof include lauroyl-Gly-His and lauroyl-Ala-His; myristoyl-Gly-His and myristoyl-Ala-His; palmitoyl-Gly-His and palmitoyl-Ala-His; and stearoyl-Gly-His and stearoyl-Ala-His.

Examples of other low-molecular compounds containing a hydrophobic moiety and a hydrophilic moiety can include a lipid peptide of Formula (2).

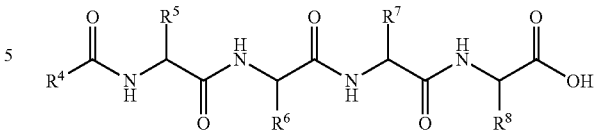

In Formula (2), $R^4$ is a $C_{9-23}$ aliphatic group, preferable specific examples of which include the same groups as previously mentioned for $R^1$.

$R^5$ to $R^8$ are a hydrogen atom, a $C_{1-4}$ alkyl group that optionally contains a $C_{1-2}$ branched chain, or a —$(CH_2)_n$—X group, and at least one or more of $R^5$ to $R^8$ is(are) a —$(CH_2)_n$—X group. n is a number of 1 to 4, and X is an amino group, a guanidino group, a —$CONH_2$ group, a 5-membered ring optionally containing 1 to 3 nitrogen atoms, a 6-membered ring optionally containing 1 to 3 nitrogen atoms, or a condensed heterocycle that contains a 5-membered ring and a 6-membered ring optionally containing 1 to 3 nitrogen atoms. Preferable specific examples of $R^5$ to $R^8$ include the same groups as previously mentioned for $R^2$ and $R^3$.

As for the compound of Formula (2), examples of lipid peptides that are particularly, most preferable as the low-molecular gelator include lauroyl-Gly-Gly-Gly-His, (Gly-Gly-Gly-His=SEQ ID No:1), myristoyl-Gly-Gly-Gly-His, palmitoyl-Gly-Gly-Gly-His, palmitoyl-Gly-Gly-His-Gly, (Gly-Gly-His-Gly=SEQ ID NO:2), palmitoyl-Gly-His-Gly-Gly, (Gly-His-Gly-Gly=SEQ ID NO:3), palmitoyl-His-Gly-Gly-Gly (His-Gly-Gly-Gly=SEQ ID NO:4), stearoyl-Gly-Gly-Gly-His, and the like.

The gelled aqueous medium used in the spray base material of the present invention is formed to contain the low-molecular gelator and an aqueous medium (solvent).

The solvent is not particularly limited, provided that the solvent does not interfere with fiber formation and hydrogelation of the low-molecular gelator, and water, an alcohol, a mixed solvent of water and alcohol, or a mixed solvent of water and a water-soluble organic solvent can be preferably used. More preferable are water or a mixed solvent of water and an alcohol, and further preferable is water.

The alcohol is preferably a water-soluble alcohol that freely dissolves in water, is more preferably a $C_{1-6}$ alcohol, is further preferably methanol, ethanol, 2-propanol, isobutanol, propylene glycol, 1,3-butanediol, or glycerin, and is further particularly preferably ethanol, 2-propanol, propylene glycol, 1,3-butanediol, glycerin, or polyethylene glycol.

The water-soluble organic solvent is organic solvents other than alcohol and means organic solvents that dissolve in water at any proportion. Examples of the water-soluble organic solvents used include acetone, dioxanes, and the like.

The gelled aqueous medium may contain an acid and/or a salt. The acid and the salt may be added at any step during the course of hydrogel formation, and are preferably added to the solvent to make a solution before addition of hydrogelator.

Although a plurality of acids and salts may be added or a mixture of an acid and a salt may be added, 1 to 3 acids or salts are preferably added. Two salts, or 1 to 2 acids and 1 to 2 salts are preferably added so as to impart a buffering capacity to the solution.

The acid is an inorganic acid or an organic acid. Examples of preferable inorganic acids include carbonic acid, sulfuric acid, and phosphoric acid. More preferable is phosphoric acid, and further preferable is phosphoric acid. Examples of preferable organic acids include acetic acid, citric acid, succinic acid, and lactic acid. More preferable is lactic acid.

The salt is an inorganic salt or an organic salt. Examples of preferable inorganic salts include inorganic lactates, inorganic carbonates, inorganic sulfates, and inorganic phosphates. More preferable are potassium lactate, sodium lactate, calcium carbonate, sodium carbonate, potassium carbonate, sodium sulfate, potassium sulfate, sodium sulfate, magnesium sulfate, potassium phosphate, sodium phosphate, disodium hydrogen phosphate, and sodium dihydrogen phosphate, and further preferable are potassium lactate, sodium lactate, calcium carbonate, magnesium sulfate, disodium hydrogen phosphate, and sodium dihydrogen phosphate. Examples of preferable organic salts include organic amine hydrochlorides and organic amine acetates. More preferable are ethylenediamine hydrochloride, ethylenediamine tetraacetate, and trishydroxymethylaminomethane hydrochloride.

As for the spray base material of the present invention, the concentration of the low-molecular gelator in the gelled aqueous medium is 0.0001 to 20% (w/v), is preferably 0.05 to 10 (w/v), and is more preferably 0.1 to 5% (w/v).

Examples of physiologically active substances that can be contained in the spray base material of the present invention include anti-inflammatory and immune agents such as indomethacin, antimicrobial and antiseptic agents such as benzalkonium, and anti-aging agents such as EGF (epidermal growth factor), FGF (fibroblast growth factor), collagen, and hyaluronic acid.

Examples of functional substances can include perfumes and refrigerants such as menthol, camphor, and rosemary, pigments, dyes, colorants, and colors such as brilliant blue, fluorescein, carotin, riboflavin, bentonite, silica, titanium oxide, talc, and potassium carbonate, vitamins such as ascorbic acid, skin-lightening agents such as tocophenol, moisturizing factors such as amino acids, urea, and ceramide, and the like.

The present invention also relates to a sol obtained by, for example, mechanically disintegrating an aqueous medium gelled by a low-molecular gelator in the medium, in which the low-molecular gelator includes one, two, or more compounds selected from a group consisting of low-molecular compounds that can gel the aqueous medium via self-assembly, and a spray base material containing the sol.

The sol is preferably obtained by mechanically disintegrating a gelled aqueous medium that is formed to contain the low-molecular gelator mentioned above, preferably a low-molecular gelator including one, two, or more compounds selected from a group consisting of the low-molecular compounds (lipid peptides) of Formula (1) and Formula (2), and the aqueous medium (solvent) mentioned above.

[Gel Formation Mechanism]

When the low-molecular gelator used in the spray base material of the present invention, in particular the low-molecular compound (lipid peptide) of Formula (1) (or Formula (2)), is added to an aqueous solution or an alcohol solution system, the peptide moieties in Formula (1) form an intermolecular non-covalent bond via a hydrogen bond and, on the other hand, the lipid moieties in Formula (1) self-assemble (also called self-organize) via hydrophobical packing, thereby forming fibers. The shape of the fiber is not limited, and examples thereof include a tubular shape and a platy shape.

For reference, a conceptual view of self-assembly and gelation of a lipid peptide is shown in FIG. 1 (however, not all the lipid peptides in the spray base material of the present invention necessarily undergo the self-assembly and the gelation shown in FIG. 1). A lipid peptide molecule (a) assembles with each other (b) with its lipid moiety that is a hydrophobic moiety arranged inside to form a fiber (c) via self-assembly.

To form the fiber, one low-molecular hydrogelator may be used or two or more low-molecular hydrogelators may be used in combination. Preferable is one or two, and further preferable is one. Using two low-molecular hydrogelators, a characteristic that is different from the characteristic obtained using one low-molecular hydrogelator can be expected to be obtained.

When the low-molecular gelator used in the spray base material of the present invention is mixed with a surfactant or an oil to cause self-assembly, a fiber can be formed. Examples of the surfactants include anionic surfactants, nonionic surfactants, and cationic surfactants. Examples of the oil include mineral oils, squalane, olive oil, and the like.

The fiber that is formed in an aqueous solution or an aqueous alcohol solution, etc. forms a three-dimensional network structure (see (d) in FIG. 1, for example), and then a non-covalent bond is formed between the hydrophilic moiety (peptide moiety) on the surface of the fiber and the aqueous solvent to cause swelling. The swelling leads the entire water-soluble system or the aqueous alcohol solution as a whole to gel, thereby achieving gelation of the aqueous medium.

As described above, the low-molecular gelator used in the spray base material of the present invention forms a self-assembly in the aqueous medium not only when the aqueous medium is gel but also when the aqueous medium is a sol and even when the addition amount of the low-molecular gelator is insufficient to achieve gelation, and maintains the self-assembly after spraying.

Therefore, the spray base material of the present invention can achieve spraying without scattering off an object to a great extent, can uniformly coat the surface of the object, and can achieve spraying without causing dripping from a coated adhesive surface.

Containing a low-molecular gelator that includes natural raw materials such as fatty acids and amino acids, the spray base material of the present invention can be safely used for coating a skin surface and the like with a sense of security.

Therefore, the spray base material of the present invention has wide applications in spray base materials for wound dressings that are capable of recognizing an affected area or a lesion area, anti-adhesion membranes, drug-quick delivery systems, skin care products, hair care products, pharmaceuticals for external use, fragrances, deodorants, insect repellents, insecticides, and agrochemicals, base materials for detergents, paints, antistatic coatings, and preservatives, base materials for forming coatings and thin films, and the like.

EXAMPLES

The present invention will be specifically described with Examples and Comparative Examples. The present invention is, however, not limited to the following Examples.

Abbreviations to be used in the following Examples mean as follows.

Gly: glycine

His: histidine

HBTU: 2-(1-H-benzotriazol-1-yl)-1,1,3,3-tetramethyluronium-hexafluorophosphate (Watanabe Chemical Industries, Ltd.)

HOBt: 1-hydroxy-benzotriazole (Peptide Institute, Inc.)

DMF: dimethylformamide

NMP: N-methyl-2-pyrrolidone

DIPEA: N,N-diisopropylethylamine (TOKYO CHEMICAL INDUSTRY CO., LTD.)

TFA: trifluoroacetic acid (Watanabe Chemical Industries, LTD.)

TIS: triisopropylsilane (Watanabe Chemical Industries, LTD.)

DMSO: dimethylsulfoxide

WSCD: 1-ethyl-3-(3-dimethylaminopropyl)carbodiimide

"Me" is a methyl group, "Et" is an ethyl group, "tBu" is a Cert-butyl group, "Ac" is an acetyl group, and "Trt" is a trityl group (a protecting group).

[Synthesis of Lipid Peptide]

A lipid peptide was synthesized by the Fmoc solid phase peptide synthesis method shown below. As a resin, an amino acid-Barlos Resin was mainly used. The synthesis scale adopted was 0.3 mmol.

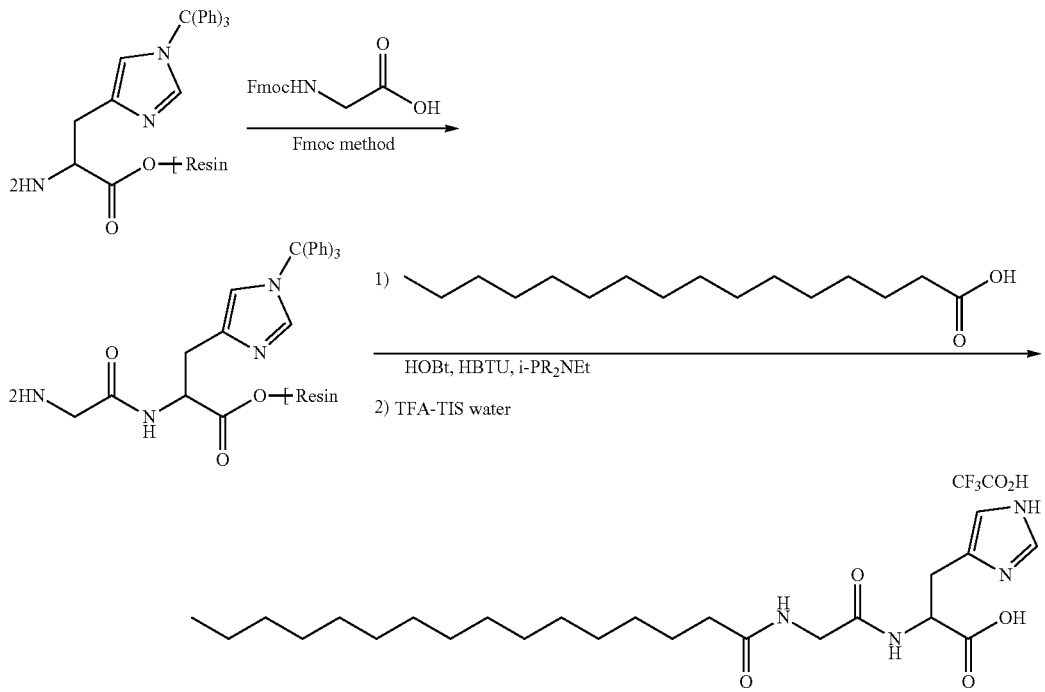

Synthesis Example 1

Solid Phase Synthesis of N-palmitoyl-Gly-His Trifluoroacetic Acid (TFA) Salt A reaction vessel into which 163 mg (0.125 mmol, 0.77 mmol/g) of an H-His(Trt)-Trt(2-Cl) resin (Watanabe Chemical Industries, LTD.) was added was installed in a peptide synthesis device, and condensation was performed with 149 mg (4 eq) of Fmoc-Gly-OH (Watanabe Chemical Industries, LTD.) by the Fmoc method to obtain an H-Gly-His(TrO-Trt (2-Cl) resin.

The peptide resin obtained was transferred to a manually operated reaction device while wet and, thereto, 160 mg (5 eq) of palmitic acid (manufactured by Aldrich Corp.), 85 mg (5 eq) of HOBt, 235 mg (5 eq) of HBTU, 1 ml of DMF, and 2 ml of NMP were added. The mixture was then stirred, and 0.22 ml of DIPEA was further added thereto. After stirring for 1 hour, a small amount of the resin was taken as a sample to confirm the completion of the reaction. After filtering off the reaction fluid, the resin was sequentially washed with NMP and then with methanol, and was dried under reduced pressure to obtain 187 mg of an N-palmitoyl-Gly-His(Trt)-Trt(2-Cl) resin.

The dry resin as a whole was treated with 1.8 ml of TFA-TIS-water (95:2.5:2.5), and 37 mg of the crude peptide obtained was purified by a preparative HPLC system using an ODS column. An eluted fraction liquid of a desired purity was collected, acetonitrile was distilled off, and then lyophilization was performed to obtain 32 mg of N-palmitoyl-Gly-His (TFA salt).

$^1$NMR (300 MHz DMSO-$d_6$ δppm): 8.93 (1H, s), 8.22 (1H, d, J=8.4 Hz), 8.05 (1H, t, J=6.3 Hz), 735 (1H, s), 4.54 (1H, m), 3.65 (2H, d=5.7 Hz), 3.14 (1H, m), 2.99 (1H, m), 2.10 (2H, t, J=7.5 Hz), 1.47 (2H, m), 1.23 (24H, s), 0.85 (3H, t, J=6.6 Hz).

MS (EI) m/z: 451.4 (M$^+$+1)

HPLC purification conditions:

Column: YMC-Pack ODS-A (250×20 mm I.D.)

Flow rate: 10 ml/min

Elution: MeCN/0.1% TFA aq.

=45/55–(80 min, liner gradient)–65/35

Detection wavelength: 220 nm

Temperature: room temperature

Synthesis Example 2

Liquid Phase Synthesis of N-palmitoyl-Gly-His TFA Salt

<Synthesis of N-palmitoyl-Gly-OtBu>

Gly-tBu.HCl (8.82 g, 52.6 mmol) and palmitoyl chloride (15.2 ml, 50.1 mmol) were dissolved in 200 ml of chloroform and, to the resultant while cooled with ice with stirring, triethylamine (14.6 ml, 105 mmol) was added dropwise over 10 minutes. Subsequently, the resultant was left to gradually reach room temperature and was stirred for 15 hours. Water was added thereto for separation, and then an organic phase was washed with a saturated saline solution and dried over magnesium sulfate. After concentrated under reduced pressure, the residue was washed with hexane and was filtered to obtain 17.4 g (94%) of a desired compound as a colorless solid.

$^1$H-NMR (300 MHz DMSO-d$_6$ δppm): 8.09 (1H, t, J=6.3 Hz), 3.67 (2H, d, J=6.3 Hz), 2.09 (2H, t, J=7.8 Hz), 1.48 (21-1, m), 1.39 (9H, s), 1.23 (24H, brs), 0.85 (3H, t, J=6.9 Hz).

MS (EI) m/z: 314.3 (M+−Boc+H)

<Synthesis of N-palmitoyl-Gly>

4 M HCl/AcOEt (118 ml, 0.471 mmol) was added to N-palmitoyl-Gly-OtBu (17.4 g, 47.1 mmol), and the resultant was stirred at room temperature for 1 hour. After concentrated under reduced pressure, the residue was washed with hexane and was filtered to obtain 11.4 g (77%) of a desired compound as colorless powder.

$^1$H-NMR (300 MHz DMSO-d$_6$ δppm): 12.43 (1H, brs), 8.07 (1H, t, J=6.0 Hz), 3.70 (2H, d, J=5.7 Hz), 2.09 (2H, t, J=7.8 Hz), 1.47 (2H, m), 1.23 (2411, brs), 0.85 (3H, t, J=6.9 Hz).

<Synthesis of N-palmitoyl-Gly-His(Trt)-OtBu>

His(Trt)-OtBu (15.0 g, 33.1 mmol) and HOBt.H$_2$O (5.13 g, 33.5 mmol) were added to N-palmitoyl-Gly (10.0 g, 31.9 mmol) and, to the resultant while cooled with ice with stirring, WSCD.HCl (6.42 g, 33.5 mmol) was further added. The resultant was stirred for 30 minutes while cooled with ice and for another 18 hours at room temperature. Water (500 ml) and ethyl acetate (400 ml) were added thereto for separation, and an aqueous phase was extracted with ethyl acetate (200 ml). Organic phases were combined to be sequentially washed with a saturated aqueous sodium hydrogen carbonate solution, a saturated saline solution, a 10% aqueous citric acid solution, and a saturated saline solution, and the resultant was dried over magnesium sulfate. Being concentrated under reduced pressure, 28.1 g (118%) of a desired compound was obtained as a pale yellow oil.

$^1$H-NMR (300 MHz DMSO-d$_6$ δppm): 7.77 (1H, d, J=7.8 Hz), 7.35-7.29 (10H, m), 7.13-7.07 (6H, m), 6.64-6.58 (2H, m), 4.67 (1H, m), 3.98 (2H, m), 2.98 (2H, m), 2.22 (2H, m), 1.61 (2H, m), 1.34 (9H, s), 1.25 (24H, brs), 0.87 (3H, t, J=6.6 Hz).

<Synthesis of N-palmitoyl-Gly-His TFA Salt>

To N-palmitoyl-Gly-His(Trt)-OtBu (23.0 g, 30.8 mmol) while cooled with ice, a TFA (206 ml)-TIS (10.8 ml)-H$_2$O (10.8 ml) mixture was added and the resultant was stirred at room temperature for 1 hour. After concentrated under reduced pressure, the resultant was washed with diisopropyl ether and then with diethyl ether, and was then filtered with a membrane filter. The product was reprecipitated with TFA (35 ml) diethyl ether (800 ml), and the resultant was dried under reduced pressure to obtain 16.2 g (93%) of a desired compound.

$^1$H-NMR (300 MHz DMSO-d$_6$ δppm): 8.96 (1H, s), 8.21 (1H, d, J=8.4 Hz), 8.04 (1H, t, J=6.0 Hz), 7.36 (1H, s,), 4.57-4.50 (1H, m), 3.65 (2H, d=6, 3 Hz), 3.14 (1H, m), 2.99 (1H, m), 2.10 (2H, t, J=7.5 Hz), 1.47 (2H, m), 1.23 (24H, s), 0.85 (3H, t, J=6.6 Hz).

MS (EI) m/z: 451.4 (M$^+$+1)

Synthesis Example 3

Method for Protecting-Group-Free Synthesis of N-palmitoyl-Gly-His TFA Salt

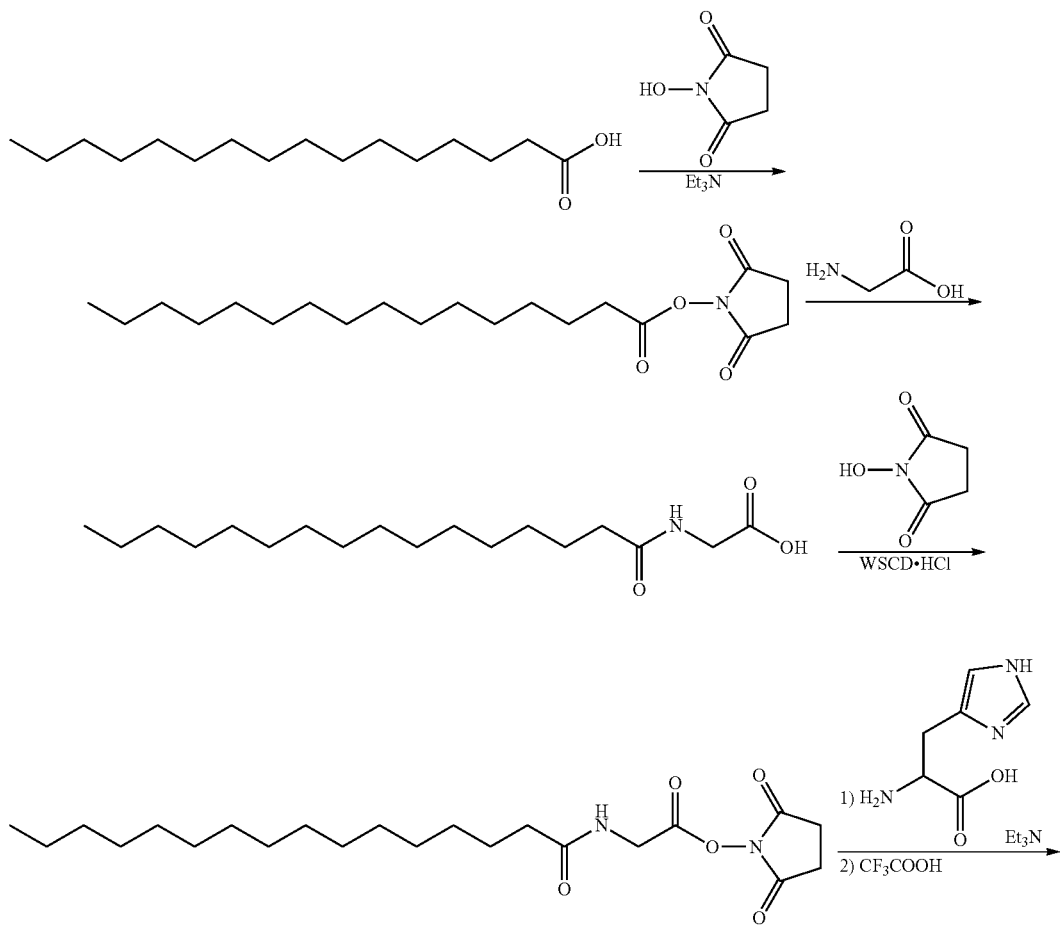

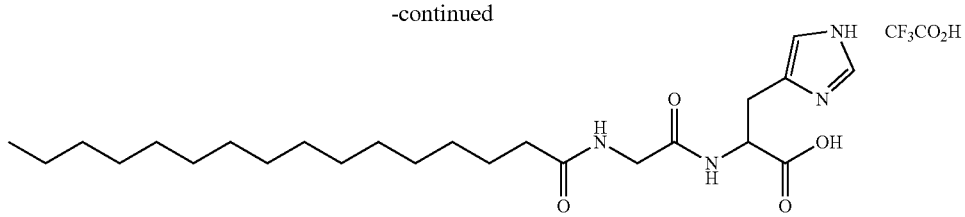

<Synthesis of N-palmitoyloxy-succinimide>

To a solution of palmitoyl chloride (165 ml, 0.544 mol) in 1 L of chloroform while cooled with ice with stirring, N-hydroxysuccinimide (69.8 g, 0.598 mol) was added by a small amount at a time, and triethylamine (83.1 ml, 0.598 mol) was added dropwise thereto over 30 minutes. The resultant was stirred for 30 minutes while cooled with ice and for another 7 hours during which the resultant gradually reached room temperature. After washed with water (500 ml×3), the resultant was dried over magnesium sulfate and was then concentrated under reduced pressure to obtain 260.3 g (quant) of a colorless solid.

$^1$H-NMR (300 MHz DMSO-$d_6$ δppm): 2.80 (4H, s), 2.65 (2H, t, J=7.2 Hz), 1.61 (2H, quintet, J=7.2 Hz), 1.24 (24H, s), 0.85 (3H, t, J=6.3 Hz).

<Synthesis of N-palmitoyl-Gly>

The N-palmitoyloxy-succinimide synthesized above as a whole (260.3 g) was suspended in 750 ml of DMF and, to the resultant while cooled with ice with stirring, Gly (56.3 g, 0.750 mol) and triethylamine (83.2 ml, 0.598 mol) dissolved in 250 ml of water were added dropwise. The resultant was stirred for another 30 minutes while cooled with ice and for another 15 hours during which the resultant gradually reached room temperature. 100 ml of 6 N hydrochloric acid was dissolved in 1 L of water to prepare an aqueous solution of pH 3 and, to the resultant while cooled with ice with stirring, the reaction solution containing N-palmitoyloxy-succinimide was added dropwise to precipitate a solid, which was filtered. The resultant was washed with 2 L of water and then with 1 L of hexane, and was then collected to obtain 114 g (67%) of a desired compound.

$^1$H-NMR (300 MHz DMSO-$d_6$ δppm): 8.10 (1H, t, J=6 Hz), 3.71 (2H, d, J=6 Hz), 2.10 (2H, t, J=7.2 Hz), 1.48 (2H, m), 1.23 (24H, s), 0.85 (3H, t, J=6.3 Hz).

<Synthesis of N-palmitoyloxy-glycyloxysuccinimide>

114 g (0.364 mol) of the N-palmitoyl-Gly synthesized above and N-hydroxysuccinimide (44.0 g, 0.382 mol) were suspended in 620 ml of DMF and, to the resultant while cooled with ice with stirring, WSCD hydrochloride (73.2 g, 0.382 mol) was added. The resultant was stirred for 30 minutes while cooled with ice and then for another 20 hours at room temperature. 1.5 L of ice water was added thereto to filter insoluble matter, the resultant was washed with 5 L of water and then with 1.5 L of an ether, and the obtained solid matter was dried under reduced pressure to quantitatively obtain 198 g of a colorless solid.

$^1$H-NMR (300 MHz DMSO-$d_6$ δppm): 8.46 (1H, t, J=5.7 Hz), 422 (2H, d, J=5.7 Hz), 2.89 (4H, s), 2.13 (2H, t, J=7.2 Hz), 1.49 (2H, m), 1.23 (24H, s), 0.85 (3H, t, J=6.3 Hz).

<Synthesis of N-palmitoyl-Gly-His TFA Salt>

198 g of the N-palmitoyloxy-glycyloxysuccinimide synthesized above as a whole was suspended in DMF and, to the resultant while cooled with ice with stirring, 113 g (0.728 mol) of L-histidine and 55.6 ml (0.400 mol) of triethylamine suspended in 350 ml of water were added. Subsequently, the resultant was stirred for 30 minutes while cooled with ice, and then the temperature was raised to room temperature to continue stirring for another 17 hours. The precipitated solid was filtered as it was to obtain a solid. The resultant was added to a mixed solution of 120 ml of trifluoroacetic acid and 1.5 L of ice water and was then stirred, and subsequently insoluble matter was filtered. The obtained solid was placed in a jug to be washed with 2 L of water three times, and was subsequently dried under reduced pressure. The obtained dry solid was dissolved in 400 ml of trifluoroacetic acid, and a small amount of insoluble matter was filtered off with a membrane filter. The filtrate was concentrated under reduced pressure to about half the amount, which was then washed with diethyl ether, and the solid was dried under reduced pressure. The solid was washed with water appropriate times, and the obtained solid was dried under reduced pressure to obtain 112 g (54%) of a colorless solid.

Synthesis Example 4

Synthesis of N-palmitoyl-Gly-His (Free Form)

175 mL of DMF was added to 2.0 g (4.86 mmol) of N-palmitoyloxy-glycyloxysuccinimide that was a synthetic intermediate in Synthesis Example 3, and the resultant was cooled in an ice bath. Subsequently, 45 mL of water, 0.74 mL (5.46 mmol, 1.1 eq) of triethylamine, and 1.50 g (9.72 mmol, 2.0 eq) of H-L-His-OH were added thereto to allow a reaction to proceed for 30 minutes. The reaction solution was then left to reach room temperature and the reaction was allowed to proceed at room temperature for 23.5 hours.

After the completion of the reaction, the reaction solution (gel) was centrifuged (4° C., 10,000 rpm, 15 minutes) to perform lyophilization (7 hours×2). The gel product from which supernatant was removed was dissolved in 350 mL of methanol, insoluble matter was filtrated, and the filtrate was concentrated under reduced pressure to obtain a liquid (A).

On the other hand, the supernatant (DMF/aqueous phase) resulting from centrifugation was cooled in a refrigerator for 15 hours and was centrifuged (4° C., 10,000 rpm, 25 minutes), and the supernatant was then removed to perform lyophilization (7 hours×3). Subsequently, the resultant was dissolved in 250 mL of methanol, and insoluble matter was filtrated to obtain a liquid (B).

The liquid (B) was added to the liquid (A), and the resultant was concentrated under reduced pressure and was washed with 150 mL of chloroform and 150 mL of water to obtain 698.3 mg (32%) of a white solid.

$^1$H-NMR (300 MHz DMSO-$d_6$ δppm): 8.12 (1H, d, J=7.8 Hz), 8.06 (1H, t, J=5.7 Hz), 7.56 (1H, s), 6.81 (1H, s), 4.38 (1H, q, J=7.8 Hz), 3.69 (2H, dd, J=5.7 Hz and J=10.2 Hz), 2.89 (2H, m), 2.20 (2H, t, J=6.9 Hz), 1.48 (2H, m), 1.23 (24H, s), 0.85 (3H, t, J=7.2 Hz)

MS (EI) m/z: 451.43 ($M^+$+1, bp)

Synthesis Example 5

Synthesis of Free Form of N-palmitoyl-Gly-His TEA Salt by Neutralization 500 mg of N-palmitoyl-Gly-His trifluoroacetate was added to a sample bottle, 10 ml of milli-Q water was added thereto, and 17.7 ml of a 0.05 M aqueous sodium hydroxide solution was then added thereto to be mixed together. The resultant was placed in a water bath at 90° C. to be completely dissolved with lightly shaking, was left to cool, and was then lyophilized to obtain a solid. The solid was washed with water appropriate times and was then dried under reduced pressure to quantitatively obtain 399 g of a neutralized product.

Example 1

1% (w/v), Phosphate Buffer Solution (1)

The N-palmitoyl-Gly-His TFA salt (250.1 mg) obtained in Synthesis Example 2 was placed in a screw tube (Maruemu Corporation, No. 7) and, thereto, a phosphate buffer solution (manufactured by Wako Pure Chemical Industries, Ltd., phosphate buffer powder, 1/15 mol/L, pH=7.4, composition $Na_2HPO_4$ 7.6 g, $KH_2PO_4$ 1.8 g/L) was added to achieve a concentration of 1% (w/v) (w means mass (g) and v means volume (mL)). The resultant was heated in a dry bath incubator (manufactured by First Gene Corp.) (100° C., 10 minutes), and the obtained solution was transferred into a spray vial (Maruemu Corporation, No. 3L) to be left to cool to reach room temperature.

A state in which, after cooling down, the solution lost fluidity and did not flow down when the sample tube (the spray vial) was inverted was confirmed, and thus it was determined that the solution had been gelled.

Example 2

The gel obtained in Example 1 was vibrated for 10 minutes in a microtube mixer (manufactured by Nissin Scientific Corporation) at 2,600 rpm to obtain a sal (the gel was mechanically disintegrated into a sol.).

Example 3

0.5% (w/v), Ultrapure Water (1)

The N-palmitoyl-Gly-His TFA salt (232.3 mg) obtained in Synthesis Example 2 was placed in a screw tube (Maruemu Corporation, No. 7) and, thereto, ultrapure water (manufactured by Kurita Water Industries Ltd.) was added to achieve a concentration of 0.5% (w/v). The resultant was heated in a dry bath incubator (manufactured by First Gene Corp.) (100° C., 10 minutes), and the obtained solution was transferred into a spray vial (Maruemu Corporation, No. 3L) to be left to cool to reach room temperature.

A state in which, after cooling down, the solution lost fluidity and did not flow down when the sample tube was inverted was confirmed, and thus it was determined that the solution had been gelled.

Example 4

The gel obtained in Example 3 was vibrated for 10 minutes in a microtube mixer (manufactured by Nissin Scientific Corporation) at 2,600 rpm to obtain a sol (the gel was mechanically disintegrated into a sal.).

Example 5

3% (w/v), Aqueous Ethanol Solution (70% (v/v))

The N-palmitoyl-Gly-His TFA salt (300.0 mg) obtained in Synthesis Example 2 was placed in a spray vial (Maruemu Corporation, No. 3L) and, thereto, a 70% (v/v) aqueous ethanol (EtOH) solution was added to achieve a concentration of 3% (w/v). The resultant underwent sonication (manufactured by Iuchi Seieido, K.K. (current As One Corporation), 38 kHz, 200 w) for 1 hour to be left still standing at room temperature overnight.

A state in which the solution lost fluidity and did not flow down when the sample tube was inverted was confirmed, and thus it was determined that the solution had been gelled.

Example 6

The gel obtained in Example 5 was vibrated for 10 minutes in a microtube mixer (manufactured by Nissin Scientific Corporation) at 2,600 rpm to obtain a sol. (the gel was mechanically disintegrated into a sol).

Example 7

0.1% (w/v), Aqueous Glycerin Solution (70% (w/w))

The free form N-palmitoyl-Gly-His (10.0 mg) obtained in Synthesis Example 4 was placed in a screw tube (Maruemu Corporation, No. 7) and, thereto, a 70% (w/w) aqueous glycerin solution was added to achieve a concentration of 0.1% (w/v). The resultant was heated in a dry bath incubator (manufactured by First Gene Corp.) (95° C., 30 minutes), and the obtained solution was transferred into a spray vial (Maruemu Corporation, No. 3L) to be left to cool to reach room temperature.

A state in which, after cooling down, the solution lost fluidity and did not flow down when the sample tube was inverted was confirmed, and thus it was determined that the solution had been gelled.

Example 8

0.1% (w/v), Aqueous Glycerin Solution (50% (w/w))

The free form N-palmitoyl-Gly-His (20.0 mg) obtained in Synthesis Example 4 was placed in a screw tube (Maruemu Corporation, No. 7) and, thereto, a 50% (w/w) aqueous glycerin solution was added to achieve a concentration of 0.1% (w/v). The resultant was heated in a dry bath incubator (manufactured by First Gene Corp.) (95° C., 30 minutes), and the obtained solution was transferred into a spray vial (Maruemu Corporation, No. 3L) to be left to cool to reach room temperature.

A state in which, after cooling down, the solution lost fluidity and did not flow down when the sample tube was inverted was confirmed, and thus it was determined that the solution had been gelled.

Example 9

025% (w/v), Aqueous Propylene Glycol Solution (70% (w/w))

The free form N-palmitoyl-Gly-His (19.9 mg) obtained in Synthesis Example 4 was placed in a screw tube (Maruemu Corporation, No. 7) and, thereto, a 70% (w/w) aqueous propylene glycol solution was added to achieve a concentration of 0.25% (w/v). The resultant was heated in a dry bath incubator (manufactured by First Gene Corp.) (75° C., 10 minutes), and the obtained solution was transferred into a spray vial (Maruemu Corporation, No. 3L) to be left to cool to reach room temperature.

A state in which, after cooling down, the solution lost fluidity and did not flow down when the sample tube was inverted was confirmed, and thus it was determined that the solution had been gelled.

Example 10

2% (w/v), Aqueous 1,3-butanediol Solution (70% (w/w))

The free form N-palmitoyl-Gly-His (15.0 mg) obtained in Synthesis Example 4 was placed in a screw tube (Maruemu Corporation, No. 7) and, thereto, a 70% (w/w) aqueous 1,3-butanediol solution was added to achieve a concentration of 2% (w/v). The resultant was heated in a dry bath incubator (manufactured by First Gene Corp.) (95° C., 30 minutes), and the obtained solution was transferred into a spray vial (Maruemu Corporation, No. 3L) to be left to cool to reach room temperature.

A state in which, after cooling down, the solution lost fluidity and did not flow down when the sample tube was inverted was confirmed, and thus it was determined that the solution had been gelled.

Example 11

0.5% (w/v), Aqueous Ethanol Solution (50% (w/w))

The free form N-palmitoyl-Gly-His (50.2 mg) obtained in Synthesis Example 4 was placed in a screw tube (Maruemu Corporation, No. 7) and, thereto, a 50% (w/w) aqueous ethanol solution was added to achieve a concentration of 0.5% (w/v). The resultant was heated in a dry bath incubator (manufactured by First Gene Corp.) (100° C., 3 minutes), and the obtained solution was transferred into a spray vial (Maruemu Corporation, No. 3L) to be left to cool to reach room temperature.

A state in which, after cooling down, the solution lost fluidity and did not flow down when the sample tube was inverted was confirmed, and thus it was determined that the solution had been gelled.

Example 12

2% (w/v), Aqueous Ethanol Solution (50% (w/w))

The free form N-palmitoyl-Gly-His (200 mg) obtained in Synthesis Example 4 was placed in a screw tube (Maruemu Corporation, No, 7) and, thereto, a 50% (w/w) aqueous ethanol solution was added to achieve a concentration of 2% (w/v). The resultant was heated in a dry bath incubator (manufactured by First Gene Corp.) (100° C., 3 minutes), and the obtained solution was transferred into a spray vial (Maruemu Corporation, No. 3L) to be left to cool to reach room temperature.

A state in which, after cooling down, the solution lost fluidity and did not flow down when the sample tube was inverted was confirmed, and thus it was determined that the solution had been gelled.

Example 13

1% (w/v), Ultrapure Water (2)

The free form N-palmitoyl-Gly-His (50.0 mg) obtained in Synthesis Example 4 was placed in a screw tube (Maruemu Corporation, No. 7) and, thereto, ultrapure water (manufactured by Kurita Water Industries Ltd.) was added to achieve a concentration of 1% (w/v). The resultant was heated in a dry bath incubator (manufactured by First Gene Corp.) (110° C., 10 minutes), and the obtained solution was transferred into a spray vial (Maruemu Corporation, No. 3L) to be left to cool to reach room temperature.

A state in which, after cooling down, the solution lost fluidity and did not flow down when the sample tube was inverted was confirmed, and thus it was determined that the solution had been gelled.

Example 14

2% (w/v), Ultrapure Water (3)

The free form N-palmitoyl-Gly-His (100 mg) obtained in Synthesis Example 4 was placed in a screw tube (Maruemu Corporation, No. 7) and, thereto, ultrapure water (manufactured by Kurita Water Industries Ltd.) was added to achieve a concentration of 2% (w/v). The resultant was heated in a dry bath incubator (manufactured by First Gene Corp.) (110° C., 10 minutes), and the obtained solution was transferred into a spray vial (Maruemu Corporation, No. 3L) to be left to cool to reach room temperature.

A state in which, after cooling down, the solution lost fluidity and did not flow down when the sample tube was inverted was confirmed, and thus it was determined that the solution had been gelled.

Example 15

1% (w/v), Phosphate Buffer Solution (2)

The free form N-palmitoyl-Gly-His (50.4 mg) obtained in Synthesis Example 4 was placed in a screw tube (Maruemu Corporation, No. 7) and, thereto, a phosphate buffer solution (manufactured by Wako Pure Chemical Industries, Ltd., phosphate buffer powder, 1/15 mol/L, pH=7.4, composition: $Na_2HPO_4$ 7.6 g, $KH_2PO_4$ 1.8 g/L) was added to achieve a concentration of 1% (w/v). The resultant was heated in a dry bath incubator (manufactured by First Gene Corp.) (100° C., 5 minutes), and the obtained solution was transferred into a spray vial (Maruemu Corporation, No. 3L) to be left to cool to reach room temperature.

A state in which, after cooling down, the solution lost fluidity and did not flow down when the sample tube was inverted was confirmed, and thus it was determined that the solution had been gelled.

Example 16

0.25% (w/v), Aqueous Propylene Glycol Solution (65% (w/w)) (Added with Lactic Acid and Potassium Lactate)

The free form N-palmitoyl-Gly-His (25 mg) obtained in Synthesis Example 4 was placed in a screw tube (Maruemu Corporation, No. 7) and, thereto, a 65% (w/w) aqueous propylene glycol solution was added to achieve a concentration of 0.25% (w/v). Thereto, potassium lactate:lactic acid (95:5

(in a weight ratio)) was further added to reach a concentration of 5% (w/w) relative to the entire solution. The resultant was heated in a dry bath incubator (manufactured by First Gene Corp.) at 75° C. for 10 minutes, and the obtained solution was transferred into a spray vial (Maruemu Corporation, No. 3L) to be left to cool to reach room temperature.

A state in which, after cooling down, the solution lost fluidity and did not flow down when the sample tube was inverted was confirmed, and thus it was determined that the solution had been gelled.

Example 17

0.2% (w/v), Aqueous Propylene Glycol Solution (65% (w/w)) (Added with Lactic Acid and Potassium Lactate)

The free form N-palmitoyl-Gly-His (80 mg) obtained in Synthesis Example 4 was placed in a screw tube (Maruemu Corporation, No, 7) and, thereto, a 65% (w/w) aqueous propylene glycol solution was added to achieve a concentration of 0.2% (w/v). Thereto, potassium lactate:lactic acid (95:5 (in a weight ratio)) was further added to reach a concentration of 5% (w/w) relative to the entire solution. The resultant was heated in a dry bath incubator (manufactured by First Gene Corp.) at 93° C. for 5 minutes, and the obtained solution was transferred into a spray vial (Maruemu Corporation, No. 3L) to be left to cool to reach room temperature.

A state in which, after cooling down, the solution lost fluidity and did not flow down when the sample tube was inverted was confirmed, and thus it was determined that the solution had been gelled.

Example 18

0.3% (w/w), N-palmitoyl-Gly-Gly-Gly-His (Gly-Gly-Gly-His=SEQ ID NO:1 TFA salt (ultrapure water)

By referring to the process described in International Publication No. WO 2009/005151 pamphlet, an N-palmitoyl-Gly-Gly-Gly-His (Gly-Gly-Gly-His=SEQ ID NO:1) TFA salt was synthesized.

The N-palmitoyl-Gly-Gly-Gly-His (Gly-Gly-Gly-His=SEQ ID NO:1) TFA salt (81.6 mg) obtained was placed in a screw tube (Maruemu Corporation No. 7) and, thereto, ultrapure water (manufactured by Kurita Water Industries Ltd.) was added to achieve a concentration of 0.3% (w/v). The resultant was heated in a dry bath incubator (manufactured by First Gene Corp.) (100° C., 10 minutes), and the obtained solution was transferred into a spray vial (Maruemu Corporation, No. 3L) to be cooled to reach room temperature.

A state in which, after cooling down, the solution lost fluidity and did not flow down when the sample tube was inverted was confirmed, and thus it was determined that the solution had been gelled.

Example 19

0.3% (w/w), N-palmitoyl-Gly-Gly-Gly-His (Gly-Gly-Gly-His=SEQ ID NO:1) TFA salt (phosphate buffer solution)

The N-palmitoyl-Gly-Gly-Gly-His Gly-Gly-Gly-His=SEQ ID NO:1) TFA salt (81.6 mg) that was synthesized by referring to the process described in International Publication No. WO 2009/005151 pamphlet was placed in a screw tube (Maruemu Corporation No. 7) and, thereto, a phosphate buffer solution (manufactured by Wako Pure Chemical Industries, Ltd., phosphate buffer powder, 1/15 mol/L, pH =7.4, composition: $Na_2HPO_4$ 7.6 g, $KH_2PO_4$ 1.8 g/L) was added to achieve a concentration of 0.3% (w/v). The resultant was heated in a dry bath incubator (manufactured by First Gene Corp.) (100° C., 10 minutes), and the obtained solution was transferred into a spray vial (Maruemu Corporation, No. 3L) to be cooled to reach room temperature.

A state in which, after cooling down, the solution lost fluidity and did not flow down when the sample tube was inverted was confirmed, and thus it was determined that the solution had been gelled.

Comparative Example 1

1.5% (w/v), Cellulose Gel

To 100 g of a transparent cellulose gel Cellodene 4M (cellulose gel 4 wt %, manufactured by Dai-ichi Kogyo Seiyaku Co., Ltd.), 166 g of Japanese Pharmacopoeia water was added to obtain a 1.5% (w/v) cellulose-water dispersion, which was stirred with a stirring device T.K. Mixing Analyzer MA2500 (PRIMIX Corporation) at 5,000 rpm for 240 minutes to be left still standing at room temperature.

A state in which the solution lost fluidity and did not flow down when the sample tube was inverted was confirmed, and thus it was determined that the solution had been gelled, Comparative Example 2

2% (w/v), Carboxyvinyl Polymer

To 0.252 g of a carboxyvinyl polymer Carbopol 940 (manufactured by ITO, Inc.), Japanese Pharmacopoeia water was added to achieve a concentration of 2% (w/v), and the resultant was then warmed in a water bath until dissolved. The resultant was left still standing at room temperature to gel, and gelation was confirmed.

Comparative Example 3

0.15% (w/v), Carboxyvinyl Polymer

To 0.252 g of a carboxyvinyl polymer Carbopol 940 (manufactured by ITO, Inc.), Japanese Pharmacopoeia water was added to achieve a concentration of 2% (w/v), and the resultant was then warmed in a water bath until dissolved. 15 µl of 6 N NaOH was added, and the resultant was left still standing at room temperature to gel. Gelation was confirmed.

Comparative Example 4

1.5% (w/v), Xanthan Gum

To 0.725 g of xanthan gum (manufactured by TOKYO CHEMICAL INDUSTRY CO., LTD.), Japanese Pharmacopoeia water was added to achieve a concentration of 1.5% (w/v), and the resultant was then warmed in a water bath until dissolved. The resultant was left still standing at room temperature to gel, and gelation was confirmed.

Comparative Example 5

1% (w/v), Agar-Agar

To 1.0 g of agar-agar (manufactured by ASAHI & Co., Ltd.), Japanese Pharmacopoeia water was added to achieve a concentration of 1% (w/v), and the resultant was then warmed in a water bath until dissolved. The resultant was left still standing at room temperature to gel, and gelation was confirmed.

Comparative Example 6

70% (w/w), Glycerin

To 3.0 g of glycerin (manufactured by JUN SEI CHEMICAL CO., LTD.), ultrapure water (manufactured by Kurita Water Industries Ltd.) was added and mixed so as to achieve a concentration of 70% (w/w).

Spray Application Property Evaluation (1)

Examples 20 to 27, and Comparative Examples 7 to 11

Using the gels and the sols obtained in Examples 1 to 6, Examples 18 and 19, and Comparative Examples 1 to 5, spray application was performed.

Spraying was performed three consecutive times, using a spray vial (Maruemu Corporation, No. 3L) in which the gel or the sol was placed, toward the center of a glass plate (5 cm×5 cm) that was placed 5 cm away from the nozzle tip of the spray vial (FIG. 1). After 30 seconds of observation, the longer diameter and the shorter diameter of a spray mark on the glass and the length of dripping were measured, and an average diameter was calculated using the longer diameter+ the shorter diameter. The average diameter served as an indicator of a spray application property. The results are shown in Table 1.

(Example 22, Example 23) was sprayable as gel or a sol without dripping. The gel of N-palmitoyl-Gly-Gly-Gly-His (Gly-Gly-Gly-His=SEQ ID NO:1) TFA salt that was formed using ultrapure water (Example 26) or a phosphate buffer solution (Example 27) was also sprayable as gel.

As for the average diameter of the spray mark, a spread equal to or wider than that in Comparative Example 7 in which a cellulose gel was used was observed, which means each of the spray had an effect equal or superior to that in Comparative Example 7.

On the other hand, as for the spray mark resulting from the gel containing a carboxyvinyl polymer at a concentration of 2% (w/v) or the gel containing a carboxyvinyl polymer (neutralized product) at a concentration of 0.15% (w/v) (Comparative Example 8 or Comparative Example 9), no dripping was observed, but the spray shape was a rod-like shape, which resulted in a small spread of the spray mark.

As for the spray mark resulting from the gel containing xanthan gum at a concentration of 1.5% (w/v) (Comparative Example 10), the spray shape was a rod-like shape, which resulted in a small spread of the spray mark, and dripping was observed. The gel containing agar-agar at a concentration of 1% (w/v) (Comparative Example 11) was not sprayable.

Spray Application Property Evaluation (2)

Examples 28 to 38, and Comparative Examples 12 to 14

Using the gels and the solution obtained in Examples 7 to 17 and Comparative Examples 1, 3, and 6, spray application was performed.

TABLE 1

Spray application evaluation (1)

| No. | | Gel/sol used | | Addition amount *2 | State | Average diameter (mm) | Dripping (mm) |
|---|---|---|---|---|---|---|---|
| | | Gelator *1 | Solvent | | | | |
| Example 20 | Example 1 | N-palmitoyl-Gly His | Phosphate buffer solution | 1 | Gel | 28 | 0 |
| 21 | 2 | N-palmitoyl-Gly-His | Phosphate buffer solution | 1 | Sol | 33.5 | 0 |
| 22 | 3 | N-palmitoyl-Gly-His | Ultrapure water | 0.5 | Gel | 29 | 0 |
| 23 | 4 | N-pahnitoyl-Gly-His | Ultrapure water | 0.5 | Sol | 37 | 0 |
| 24 | 5 | N-palmitoyl-Gly-His | 70% (v/v) EtOH-water | 3 | Gel | 30 | 0 |
| 25 | 6 | N-palmitoyl-Gly-His | 70% (v/v) EtOH-water | 3 | Sol | 43.3 | 0 |
| 26 | 18 | N-palmitoyl-Gly-Gly Gly-His | Ultrapure water | 0.3 | Gel | 26.0 | 17.0 |
| 27 | 19 | N-palmitoyl-Gly-Gly-Gly-His | Phosphate buffer solution | 0.3 | Gel | 25.8 | 0 |
| Comp. Example 7 | Comp. Example 1 | Cellulose gel | Ultrapure water | 1.5 | Gel | 27 | 0 |
| 8 | 2 | Carboxyvinyl polymer | Ultrapure water | 1 | Gel | 7 | 0 |
| 9 | 3 | Carboxyvinyl polymer | Ultrapure water-NaOH | 0.15 | Gel | 18.5 | 0 |
| 10 | 4 | Xanthan gum | Ultrapure water | 1.5 | Gel | 11.8 | 9.5 |
| 11 | 5 | Agar-agar | Ultrapure water | 1 | Gel | — | — |

*1 N-palmitoyl-Gly-His used in Examples 20 to 25 each and N-palmitoyl-Gly-Gly-Gly-His used in Examples 26 and 27 each are a trifluoroacetate thereof.
*2 Addition amount: (w/v)

As shown in Table 1, in a spray test, the gel or the sol of an N-palmitoyl-Gly-His (TFA salt) concentration of 3% (w/v) that was formed using 70% ethanol-water (Example 24, Example 25), the gel or the sol of an N-palmitoyl-Gly-His (TFA salt) concentration of 1% (w/v) that was formed using a phosphate buffer solution (Example 20, Example 21), or the gel or the sol of an N-palmitoyl-Gly-His (TFA salt) concentration of 0.5% (w/v) that was formed using ultrapure water Spraying was performed two consecutive times, using a spray vial (Maruemu Corporation, No. 3L) in which the gel or the solution was placed, toward the center of a glass plate (5 cm×5 cm) that was placed 3.5 cm away from the nozzle tip of the spray vial (FIG. 1). After 30 seconds of observation, the longer diameter and the shorter diameter of a spray mark on the glass and the length of dripping were measured, and an average diameter was calculated using the longer diameter+ the shorter diameter. The average diameter served as an indicator of a spray application property. The results are shown in Table 2.

(w/v) of N-palmitoyl-Gly-His TFA salt. The solution was transferred into a spray vial (Maruemu Corporation, No. 3L) to be left still standing at room temperature overnight for

TABLE 2

Spray application evaluation (2)

| No. | | | Gel/sal used | | | Average | |
|---|---|---|---|---|---|---|---|
| | | Gelator *1 | Solvent | Addition amount *2 | State | diameter (mm) | Dripping (mm) |
| Example | 28 | Example 7 N-palmitoyl-Gly His | 70% (w/w) glycerin-water | 0.1 | Gel | 21.0 | 0 |
| | 29 | 8 N-palmitoyl-Gly-His | 50% (w/w) glycerin-water | 0.1 | Gel | 28.3 | 0 |
| | 30 | 9 N-palmitoyl-Gly-His | 70% (w/w) PG-water | 0.25 | Gel | 25.0 | 0 |
| | 31 | 10 N-palmitoyl-Gly-His | 70% (w/w) 1,3 BD-water | 0.2 | Gel | 21.3 | 0 |
| | 32 | 11 N-pahnitoyl-Gly-His | 50% (w/w) EtOH-water | 0.5 | Gel | 31.8 | 0 |
| | 33 | 12 N-palmitoyl-Gly-His | 50 (w/w) % EtOH-water | 2 | Gel | 31.3 | 0 |
| | 34 | 13 N-palmitoyl-Gly-His | Ultrapure water | 1 | Gel | 26.8 | 0 |
| | 35 | 14 N-palmitoyl-Gly-His | Ultrapure water | 2 | Gel | 28.0 | 0 |
| | 36 | 15 N-palmitoyl-Gly-His | Phosphate buffer solution | 1 | Gel | 24.8 | 0 |
| | 37 | 16 N-palmitoyl-Gly-His | 65% (w/w) PG-water 5% (Potasium lactate: lactic acid) *3 | 0.25 | Gel | 23.0 | 0 |
| | 38 | 17 N-palmitoyl-Gly-His | 65% (w/w) PG-water 5% (Potasium lactate: lactic acid) *3 | 0.2 | Gel | 26.3 | 0 |
| Comp. Ex. | 12 | Comp. 1 Cellulose gel | Ultrapure water | 1.5 | Gel | 23.8 | 0 |
| | 13 | Ex. 3 Carboxyvinyl polymer | Ultrapure water + NaOH | 0.15 | Gel | 13.8 | 0 |
| | 14 | 6 — | 70% glycerin-water | — | Solution | 34.5 | 15 |

*1 N-palmitoyl-Gly-His used in Examples 28 to 38 each is in a free form.
*2 Addition amount: (w/v)
*3 65% (w/w) propylene glycol, water, 5% (w/w (relative to the entire solution)) potassium lactate: lactic acid (95:5 (in a weight ratio))

As shown in Table 2, in a spray test, the gel of N-palmitoyl-Gly-His (free form) that was formed using an aqueous glycerin solution, an aqueous propylene glycol solution, an aqueous 1,3-butanediol solution, an aqueous ethanol solution, ultrapure water, or a phosphate buffer solution (Example 28 to Example 36) was sprayable and spread without dripping. The gels of N-palmitoyl-Gly-His (free form) that were formed by adding potassium lactate and lactic acid to an aqueous propylene glycol solution (Examples 37 and 38) were also sprayable and spread without dripping.

As for the average diameter of the spray mark, a spread equal to that in Comparative Example 12 in which a cellulose gel was used was observed, which means each of the spray had an effect that is substantially equal to that in Comparative Example 12.

On the other hand, in the case of the aqueous solution prepared using glycerin (Comparative Example 13) or of the gel containing N-palmitoyl-Gly-Gly-Gly-His (Comparative Example 14), dripping was observed.

Example 39

Indomethacin-Inclusion Gel

To the N-palmitoyl-Gly-His TFA salt (300 mg) obtained in Synthesis Example 3 in an agate mortar, 8 ml of an indomethacin-containing liquid [0.375 g of indomethacin (manufactured by TOKYO CHEMICAL INDUSTRY CO., LTD.), 1.5 g of l-menthol (manufactured by JUNSEI CHEMICAL CO., LTD.), 0.005 ml of 50% benzalkonium chloride (manufactured by JUNSEI CHEMICAL CO., LTD.), 5 ml of propylene glycol (manufactured by JUNSEI CHEMICAL CO., LTD.), and 40 ml of ethanol] was gradually added, and the resultant was suspended. 2 ml of water (Japanese Pharmacopoeia water (manufactured by Kyoei Pharmaceutical Co., Ltd.)) was added thereto, and the resultant was adequately mixed to prepare a liquid containing 3% (w/v) of N-palmitoyl-Gly-His TFA salt. The solution was transferred into a spray vial (Maruemu Corporation, No. 3L) to be left still standing at room temperature overnight for gelation. Determination of gelation was made by confirming a state in which the solution lost fluidity and did not flow down when the sample tube was inverted.

Example 40

Indomethacin-Inclusion Gel

To the N-palmitoyl-Gly-His TFA salt (300 mg) obtained in Synthesis Example 3 in an agate mortar, 7 ml of an indomethacin-containing liquid [0.375 g of indomethacin (manufactured by TOKYO CHEMICAL INDUSTRY CO., LTD.), 1.5 g of l-menthol (manufactured by JUNSEI CHEMICAL CO., LTD.), 0.005 ml of 50% benzalkonium chloride (manufactured by SUNSET CHEMICAL CO., LTD.), 5 ml of propylene glycol (manufactured by JUNSEI CHEMICAL CO., LTD.), and 40 ml of ethanol] was gradually added, and the resultant was suspended. 3 ml of water (Japanese Pharmacopoeia water (manufactured by Kyoei Pharmaceutical Co., Ltd.)) was added thereto, and the resultant was adequately mixed to prepare a liquid containing 3% (w/v) of N-palmitoyl-Gly-His TFA salt. The solution was transferred into a spray vial (Maruemu Corporation, No. 3L) to be left still standing at room temperature overnight for gelation. Determination of gelation was made by confirming a state in which the solution lost fluidity and did not flow down when the sample tube was inverted.

Comparative Example 15

To 3 g of Cellodene 4M (cellulose gel 4 wt %, manufactured by Dai-ichi Kogyo Seiyaku Co., Ltd.), 7 ml of the indomethacin-containing liquid as described above or the same amount of water (Japanese Pharmacopoeia water (manufactured by Kyoei Pharmaceutical Co., Ltd.)) was added, and the resultant was stirred for 90 minutes using an IKA ULTR TURRAX stirring device and an ST20 tube for stirrer at 4,000 rpm. Heating was performed with a dry bath incubator (manufactured by First Gene Corp.).

No gelation was observed for Cellodene 4M that was mixed with the indomethacin-containing liquid.

Spray Application Property Evaluation

Example 41 and Example 42

Using the gels obtained in Example 39 and Example 40, spray application was performed.

Spraying was performed three consecutive times, using a spray vial (Maruemu Corporation, 3L) in which the gel was placed, toward the center of a glass plate (5 cm×5 cm) that was placed 5 cm away from the nozzle tip of the spray vial (FIG. 1). After 30 seconds of observation, the longer diameter and the shorter diameter of a spray mark on the glass and the length of dripping were measured, and an average diameter was calculated using the longer diameter+the shorter diameter. The average diameter served as an indicator of a spray application property. The results are shown in Table 3.

TABLE 3

Evaluation of spraying of indomethacin-inclusion gel

| | | Gelator [*1] | Addition [*2] amount | Gel used/amount of indomethacin-containing liquid Amount of indomethacin-containing liquid | Average diameter (mm) | Dripping (mm) |
|---|---|---|---|---|---|---|
| Ex. 41 | Ex. 39 | N-palmitoyl-Gly-His | 3 | 7 ml | 45.0 | 0 |
| Ex. 42 | Ex. 40 | N-palmitoyl-Gly-His | 3 | 8 ml | 44.2 | 0 |

[*1] Each N-palmitoyl-Gly-His used in Examples 41 and 42 is a trifluoroacetate thereof.
[*2] Addition amount: (w/v)

As shown in Table 3, the indomethacin-inclusion gels of a palmitoyl-Gly-His (free form) concentration of 3% (w/v) (Examples 35, 36) were sprayable without dripping.

RELATED ART DOCUMENTS

Patent Documents

Patent Document 1: Japanese Patent Application Publication No. JP-A-2001-89359
Patent Document 2: Japanese Patent Application Publication No. JP-A-2001-72999
Patent Document 3: Japanese Patent Application Publication No. JP-A-2000-351726
Patent Document 4: Japanese Patent Application Publication No, JP-A-2000-229255
Patent Document 5: Japanese Patent Application Publication No. JP-A-9-241115
Patent Document 6: Japanese Patent Application Publication No. JP-A-2000-51682
Patent Document 7: International Publication No. WO 2009/005151 pamphlet
Patent Document 8: International Publication No. WO 2009/005152 pamphlet Non-Patent Documents Non-patent Document 1: Shinji Matsumoto, Itaru Hamachi, DOJIN NEWS No. 118, 1-16 (2006)
Non-patent Document 2: Lara A. Estroff and Andrew D. Hamilton Chemical Review. 2004, 104, 1201-1217
Non-patent Document 3: Suzuki, Masahiro. Yumoto, Mariko. Mutsumi, Shirai. Hirofusa, Hanabusa, Kenji. Chemistry Letters, 33(11), 1496-1497
Non-patent Document 4: Jong Hwa Jung, Georeg John, Mitsutosish Mausda, Kaname Yoshida, Seiji Shinnkai, and Toshimi Shimizu Langumir 2001, 17, 7229-7232
Non-patent Document 5: I. Hamachi, S. Kiyonaka, S. Shinkai, Tetrahedron Lett., 2001, 42, 6141.1. Hamachi, S. Kiyonaka, S, Shinaki, Chem. Commun., 2000, 1281
Non-patent Document 6: Masahiro Suzuki, Sanae Owa, Hirofusa Shirai and Kenji Hanabusa, Tetrahedron 2007 63 7302-7308
Non-patent Document 7: Yoko Matsuzawa, Katsuyuki Ueki, Masaru Yoshida, Nobuyuki Tamaoki, Tohru Nakamura, Hideki Sakai, and Masahiko Abe, Adv. Funct. Mater. 2007, 17, 1507-1514

The invention claimed is:

1. A spray base material comprising:
an aqueous medium that is gelled by a low-molecular gelator in the medium, wherein:
the molecular weight of the low-molecular gelator is not higher that 1000; and
the low-molecular gelator is capable of gelling the aqueous medium via self-assembly and comprises at least one lipid peptide of Formula (1) or a pharmaceutically usable salt thereof:

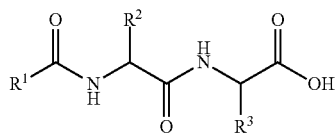

(1)

where:
$R^1$ is a $C_{9-23}$ aliphatic group,
$R^2$ is a hydrogen atom or a $C_{1-4}$ alkyl group that optionally contains a $C_{1-2}$ branched chain,
$R^3$ is a —$(CH_2)_n$—X group,
n is a number of 1 to 4, and
X is an:
 amino group,
 a guanidino group,
 a —$CONH_2$ group,
 a 5-membered ring optionally containing 1 to 3 nitrogen atoms,
 a 6-membered ring optionally containing 1 to 3 nitrogen atoms, or
 a condensed heterocycle that contains a 5-membered ring and a 6-membered ring optionally containing 1 to 3 nitrogen atoms.

2. The spray base material according to claim 1, wherein a concentration of the low-molecular gelator in the gelled aqueous medium is 0.0001 to 20% (w/v).

3. The spray base material according to claim 1, wherein the low-molecular gelator contains a hydrophobic moiety and a hydrophilic moiety.

4. The spray base material according to claim 1, wherein in Formula (1), $R^3$ is a —$(CH_2)_n$—X group, n is a number of 1 to 4, and X is an amino group, a guanidino group, a —$CONH_2$ group, a 5-membered ring optionally containing 1 or 2 nitrogen atoms, or a condensed heterocycle that contains a 5-membered ring and a 6-membered ring optionally containing 1 or 2 nitrogen atoms.

5. The spray base material according to claim 1, wherein in Formula (1), $R^1$ is a linear $C_{11-21}$ aliphatic group that optionally contains 0 to 2 unsaturated bonds.

6. The spray base material according to claim 1, wherein in Formula (1), $R^2$ is a hydrogen atom or a $C_{1-3}$ alkyl group that optionally contains a $C_1$ branched chain.

7. The spray base material according to claim 4, wherein in Formula (1), n is a number of 1 to 4 and X is an amino group, a guanidino group, or a —$CONH_2$ group, or n is 1 and X is a pyrrole group, an imidazole group, a pyrazole group, or an imidazole group.

8. The spray base material according to claim 1, further comprising a physiologically active substance or a functional substance.

9. A thin film comprising:
at least one compound having a molecular weight that is not higher that 1000 that is capable of gelling an aqueous medium via self-assembly, the at least one compound comprising at least one lipid peptide of Formula (1) or a pharmaceutically usable salt thereof:

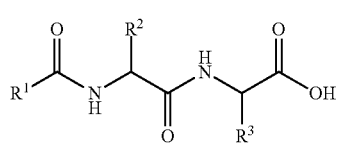

(1)

where:
- $R^1$ is a $C_{9-23}$ aliphatic group,
- $R^2$ is a hydrogen atom or a $C_{1-4}$ alkyl group that optionally contains a $C_{1-2}$ branched chain,
- $R^3$ is a —$(CH_2)_n$—X group,
- n is a number of 1 to 4, and
- X is an:
  - amino group,
  - a guanidino group,
  - a —$CONH_2$ group,
  - a 5-membered ring optionally containing 1 to 3 nitrogen atoms,
  - a 6-membered ring optionally containing 1 to 3 nitrogen atoms, or
  - a condensed heterocycle that contains a 5-membered ring and a 6-membered ring optionally containing 1 to 3 nitrogen atoms; and
- the aqueous medium.

10. The thin film according to claim 9, wherein the self-assembled at least one compound has a fibrous structure.

11. A sol obtained by mechanically disintegrating an aqueous medium that is gelled by a low-molecular gelator in the medium, wherein:
- the molecular weight of the low-molecular gelator is not higher than 1000; and
- the low-molecular gelator is capable of gelling the aqueous medium via self-assembly and comprises at least one lipid peptide of Formula (1) or a pharmaceutically usable salt thereof:

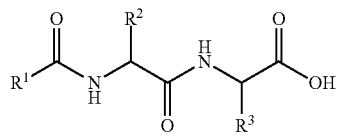

(1)

where:
- $R^1$ is a $C_{9-23}$ aliphatic group,
- $R^2$ is a hydrogen atom or a $C_{1-4}$ alkyl group that optionally contains a $C_{1-2}$ branched chain,
- $R^3$ is a —$(CH_2)_n$—X group,
- n is a number of 1 to 4, and
- X is an:
  - amino group,
  - a guanidino group,
  - a —$CONH_2$ group,
  - a 5-membered ring optionally containing 1 to 3 nitrogen atoms,
  - a 6-membered ring optionally containing 1 to 3 nitrogen atoms, or
  - a condensed heterocycle that contains a 5-membered ring and a 6-membered ring optionally containing 1 to 3 nitrogen atoms.

12. A spray base material comprising the sol of claim 11.

13. The spray base material according to claim 12, wherein in Formula (1), $R^3$ is a —$(CH_2)_n$—X group, n is a number of 1 to 4, and X is an amino group, a guanidino group, a —$CONH_2$ group, a 5-membered ring optionally containing 1 or 2 nitrogen atoms, or a condensed heterocycle that contains a 5-membered ring and a 6-membered ring optionally containing 1 or 2 nitrogen atoms.

14. The spray base material according to claim 12, wherein in Formula (1), $R^1$ is a linear $C_{11-21}$ aliphatic group that optionally contains 0 to 2 unsaturated bonds.

15. The spray base material according to claim 12, wherein in Formula (1), $R^2$ is a hydrogen atom or a $C_{1-3}$ alkyl group that optionally contains a $C_1$ branched chain.

16. The spray base material according to claim 13, wherein in Formula (1), n is a number of 1 to 4 and X is an amino group, a guanidino group, or a —$CONH_2$ group, or n is 1 and X is a pyrrole group, an imidazole group, a pyrazole group, or an imidazole group.

17. A sol comprising:
a compound of Formula (1):

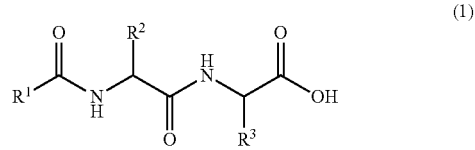

(1)

where:
- $R^1$ is a $C_{9-23}$ aliphatic group,
- $R^2$ is a hydrogen atom or a $C_{1-4}$ alkyl group that optionally contains a $C_{1-2}$ branched chain,
- $R^3$ is a —$(CH_2)_n$—X group,
- n is a number of 1 to 4, and
- X is an:
  - amino group,
  - a guanidino group,
  - a —$CONH_2$ group,
  - a 5-membered ring optionally containing 1 to 3 nitrogen atoms,
  - a 6-membered ring optionally containing 1 to 3 nitrogen atoms, or
  - a condensed heterocycle that contains a 5-membered ring and a 6-membered ring optionally containing 1 to 3 nitrogen atoms; and
- an aqueous medium;
- wherein the molecular weight of the compound of Formula (1) is not higher than 1000.

18. A spray base material comprising the sol as claimed in claim 17.

19. A process for preparing a thin film comprising applying the spray base material as claimed in claim 1 by a spray method.

* * * * *

SEQUENCE LISTING

```
<160> NUMBER OF SEQ ID NOS: 4

<210> SEQ ID NO 1
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 1

Gly Gly Gly His
1

<210> SEQ ID NO 2
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 2
```

```
Gly Gly His Gly
1

<210> SEQ ID NO 3
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 3

Gly His Gly Gly
1

<210> SEQ ID NO 4
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 4

His Gly Gly Gly
1
```